United States Patent [19]
Szajewski et al.

[11] Patent Number: 5,256,523
[45] Date of Patent: Oct. 26, 1993

[54] PHOTOGRAPHIC ELEMENT AND PROCESS

[75] Inventors: Richard P. Szajewski; Jerrold N. Poslusny, both of Rochester, N.Y.

[73] Assignee: Eastman Kodak Company, Rochester, N.Y.

[21] Appl. No.: 716,416

[22] Filed: Jun. 17, 1991

Related U.S. Application Data

[63] Continuation of Ser. No. 602,038, Oct. 23, 1990, abandoned, which is a continuation of Ser. No. 230,397, Aug. 10, 1988, abandoned.

[51] Int. Cl.$^5$ .................................................. G03C 7/00
[52] U.S. Cl. .................................... 430/362; 430/544; 430/219; 430/957; 430/382; 430/444; 430/564; 430/607; 430/611; 430/505; 430/504
[58] Field of Search ............... 430/219, 957, 544, 505, 430/382, 444, 564, 607, 611, 362, 504

[56] References Cited

U.S. PATENT DOCUMENTS

| | | |
|---|---|---|
| 3,227,554 | 1/1966 | Barr et al. ............................. 430/382 |
| 4,248,962 | 2/1981 | Lau ....................................... 430/282 |
| 4,409,323 | 10/1983 | Sato et al. ............................ 430/544 |
| 4,528,263 | 7/1985 | Sugita et al. ......................... 430/544 |
| 4,564,587 | 1/1986 | Watanabe et al. ................... 430/505 |

FOREIGN PATENT DOCUMENTS

| | | |
|---|---|---|
| 0255085 | 2/1988 | European Pat. Off. . |
| 57-093344 | 6/1982 | Japan . |
| 59-149359 | 8/1984 | Japan . |
| 1-140152 | 6/1989 | Japan ................................. 430/544 |

Primary Examiner—Charles L. Bowers, Jr.
Assistant Examiner—Thomas R. Neville
Attorney, Agent, or Firm—Peter C. Cody

[57] ABSTRACT

A compound (I) having a carrier moiety (CAR) and a releasable development inhibitor moiety (INH) capable of being released during photographic processing by means of at least one timing group (T) bonded to and releasable from the carrier moiety provides improved images in a photographic silver halide element and process when the inhibitor moiety (INH) comprises ($R^1$) a non-aromatic, sterically hindered substituent group having (a) a tertiary carbon atom bonded directly to the releasable development inhibitor moiety or (b) a secondary carbon atom bonded directly to the releasable development inhibitor moiety and wherein the secondary carbon atom is not part of an unsubstituted carbocyclic ring containing at least 6 carbon atoms. Such compounds, particularly as couplers, are useful in photographic silver halide materials and processes to provide improved acutance and interimage effects.

16 Claims, No Drawings

PHOTOGRAPHIC ELEMENT AND PROCESS

This is a continuation of application Ser. No. 602,038, filed Oct. 23, 1990, now abandoned which is a continuation of application Ser. No. 230,397, filed Aug. 10, 1988, now abandoned.

This invention relates to new photographic compounds that release a development inhibitor moiety during photographic processing and to photographic materials and processes using such compounds to provide improved acutance and interimage effects.

Various compounds, particularly couplers, are known in the photographic art that are capable of releasing a development inhibitor moiety, such as a mercaptotetrazole moiety. For example, U.S. Pat. No. 4,409,323 and U.S. Pat. No. 4,248,962 describe compounds such as couplers that release a photographically useful group, such as a development inhibitor moiety, by means of a timing group, such as a timing group that enables an intramolecular nucleophilic displacement reaction, in photographic materials. Such compounds provide advantageous control over timing and rate of release as well as rate of diffusion and distance of diffusion of the photographically useful group in the photographic material. An example of such a compound is:

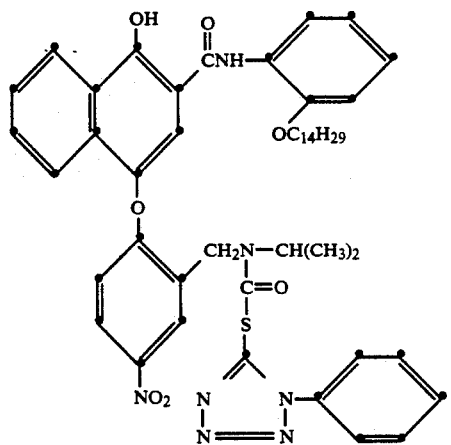

A need has existed for provision of higher acutance and higher interimage effects in a photographic silver halide material comprising such a coupler. Moreover, such compounds, particularly couplers, must not require significantly modifying the compound, from which the development inhibitor is released, in a way that would adversely affect the ultimate use for which each is intended.

The present invention solves these problems by providing a photographic element comprising a support bearing at least one photographic silver halide emulsion layer having associated therewith at least one compound (I) having a carrier moiety (CAR) and a releasable development inhibitor moiety (INH) capable of being released during photographic processing of the element by means of at least one timing group (T) bonded to and releasable from the carrier moiety, preferably a timing group that enables an intramolecular nucleophilic displacement reaction or an intramolecular elimination reaction, wherein the releasable development inhibitor moiety comprises ($R^1$) a non-aromatic, sterically hindered substituent group having (a) a tertiary carbon atom bonded directly to the releasable development inhibitor moiety or (b) a secondary carbon atom bonded directly to the releasable development inhibitor moiety and wherein the secondary carbon atom is not part of an unsubstituted carboxylic ring containing at least 6 carbon atoms. The combination of timing group (T) and the described development inhibitor moiety enable increased acutance and interimage effects upon exposure and processing of the photographic element. The compound having a carrier moiety is preferably a development inhibitor releasing coupler (DIR coupler) or an inhibitor releasing developer (IRD).

The described photographic element preferably comprises at least one dye-forming coupler. A process of developing an image in an exposed photographic element comprising a support bearing a photographic silver halide emulsion comprises the step of developing the element with a silver halide color developing agent in the presence of at least one photographic coupler and at least one compound (I) as described. A preferred compound as described is represented by the formula:

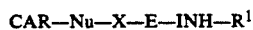

CAR—Nu—X—E—INH—$R^1$ wherein
CAR is a carrier moiety;
INH is a development inhibitor moiety containing at least one hetero atom;
Nu is a nucleophilic group attached to CAR at a position from which it is capable of being displaced as a result of reaction of CAR with oxidized color developing agent;
X is a linking group spatially relating Nu and E, upon displacement of Nu from CAR, to undergo an intramolecular nucleophilic displacement reaction that cleaves the bond between INH and E;
E is an electrophilic group attached to a hetero atom in INH; and
$R^1$ is a non-aromatic, sterically hindered substituent group having
a) a tertiary carbon atom bonded directly to INH; or
b) a secondary carbon atom bonded directly to INH and wherein the secondary carbon atom is not part of an unsubstituted carbocyclic ring containing at least 6 carbon atoms.

Another preferred compound as described is represented by the formula:

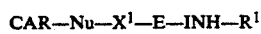

CAR—Nu—$X^1$—E—INH—$R^1$ wherein
CAR is a carrier moiety;
INH is a development inhibitor moiety containing at least one hetero atom;
Nu is a nucleophilic group attached to CAR at a position from which it is capable of being displaced as a result of reaction of CAR with oxidized color developing agent;
$X^1$ is a linking group spatially relating Nu and E, upon displacement of Nu from CAR, to undergo an intramolecular elimination reaction that cleaves the bond between INH and E, wherein X is not a pyrazolone group exemplified by

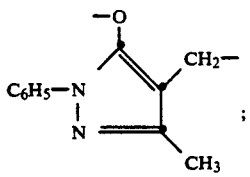

E is an electrophilic group attached to a hetero atom in INH; and

R¹ is a non-aromatic, sterically hindered substituent group having
  a) a tertiary carbon atom bonded directly to INH; or
  b) a secondary carbon atom bonded directly to INH.

The described compound (I), preferably a coupler, has a key feature that enables improved acutance to be observed in a photographic silver halide element containing such a compound upon exposure and processing. This feature is that the the inhibitor moiety is blocked and has a greater transportability in the structure of the photographic element than a prior art inhibitor moiety containing a simple phenyl group in place of the sterically hindered substituent group containing the tertiary carbon atom or secondary carbon atom as described for compound (I). The inhibitor moiety of compound (I) is substantially less absorbing to silver or silver halide than the inhibitor when released from the carrier moiety. The steric hindrance is most effective in the inhibitor moiety of compound (I) when the sterically hindered substituent group on the inhibitor moiety has (a) a tertiary carbon atom bonded directly to the inhibitor moiety, preferably a tertiary alkyl group containing 4 to 20 carbon atoms, or (b) a secondary carbon atom bonded directly to the releasable development inhibitor moiety and wherein the secondary carbon atom is not part of an unsubstituted carbocyclic ring containing at least 6 carbon atoms. These sterically hindered groups enable changes in liganding capability and as a result the described inhibitors exhibit greater degrees of interimage effects in photographic silver halide elements than otherwise is expected based on the results produced by prior art inhibitors. As a result the compound (I) enables greater acutance enhancement than prior art DIR couplers, for example those DIR couplers containing phenylmercaptotetrazole as an inhibitor moiety.

Effective image acutance enhancement is observed when the carrier moiety and the inhibitor moiety are separated by a group that enables preferred timing of release of the inhibitor moiety from the carrier moiety during photographic processing. The reaction of compound (I) with an oxidized color developing agent cleaves the bond between the carrier moiety and the timing group. Then the bond between the timing group and the inhibitor moiety is cleaved by means of an intramolecular nucleophilic displacement or elimination reaction enabling the development inhibitor moiety to perform its intended function. The sequential cleavage of these bonds is a characteristic feature of the described compound (I).

Preferred DIR couplers are represented by the formula as described wherein CAR is a coupler moiety (COUP). As used herein the terms "coupler" and "coupler compound" refer to the entire compound, including the coupler moiety, the timing groups, and the inhibitor moiety, while the term "coupler moiety" refers to the portion of the compound other than the timing groups and the inhibitor moiety.

The coupler moiety can be any moiety that will react with oxidized color developing agent to cleave the bond between the timing group and the coupler moiety. It includes coupler moieties employed in conventional color-forming couplers that yield colorless products as well as coupler moieties that yield colored products on reaction with oxidized color developing agents. Both types of coupler moieties are known to those skilled in the photographic art.

The coupler moiety can be unballasted or ballasted with an oil-soluble or fat-tail group. It can be monomeric, or it can form part of a dimeric, oligomeric or polymeric coupler, in which case more than one INH group can be contained in the coupler, or it can form part of a bis compound in which the timing and inhibitor groups form part of the link between two coupler moieties.

It will be appreciated that, depending upon the particular coupler moiety, the particular color developing agent and the type of processing, the reaction product of the coupler moiety and oxidized color developing agent can be: (1) colored and nondiffusible, in which case it will remain in the location where it is formed; (2) colored and diffusible, in which case it may be removed during processing from the location where it is formed or allowed to migrate to a different location; or (3) colorless and diffusible or nondiffusible, in which case it will not contribute to image density. In cases (2) and (3) the reaction product may be initially colored and/or nondiffusible but converted to colorless and/or diffusible products during the course of processing.

The timing group is joined to the coupler moiety at any of the positions from which groups released from couplers by reaction with oxidized color developing agent can be attached. Preferably, the timing group is attached at the coupling position of the coupler moiety so that upon reaction of the coupler with oxidized color developing agent the timing group will be displaced. However, the timing group can be in a non-coupling position of the coupler moiety from which position it will be displaced as a result of reaction of the coupler with oxidized color developing agent. In the case where the timing group is in a non-coupling position of the coupler moiety, other groups can be in the coupling position, including conventional coupling-off groups or the same or different inhibitor moieties from that contained in the described inhibitor moiety of the invention. Alternatively, the coupler moiety can have a timing and inhibitor group in each of the coupling position and a non-coupling position. Accordingly, couplers of this invention can release more than one mole of inhibitor per mole of coupler. The inhibitor can be the same or different and can be released at the same or different times and rates.

The timing group (T) can be any organic group which will serve to connect COUP to the inhibitor moiety and which, after cleavage from COUP, will cleave from the inhibitor moiety such as by an intramolecular nucleophilic displacement reaction of the type described in, for example, U.S. Pat. No. 4,248,962, or an intramolecular elimination reaction, such as of the type described in U.S. Pat. No. 4,409,323. The timing group (T) optionally can comprise two or more sequential timing groups, such as described in European Patent Application 255,085 and U.S. Pat. No. 4,698,297.

As used herein, the term "intramolecular nucleophilic displacement reaction" refers to a reaction in which a nucleophilic center of a compound reacts directly, or indirectly through an intervening molecule, at another site on the compound, which is an electrophilic center, to effect displacement of a group or atom attached to the electrophilic center. Such compounds have a nucleophilic group and electrophilic group spatially related by the configuration of the molecule to promote reactive proximity. Preferably the nucleophilic group and the electrophilic group are located in the compound so that a cyclic organic ring, or a transient cyclic organic ring, can be easily formed by an intramolecular reaction involving the nucleophilic center and the electrophilic center.

A nucleophilic group (Nu) is understood to be a grouping of atoms one of which is electron rich. This atom is referred to as the nucleophilic center. An electrophilic group (E) is understood to be a grouping of atoms one of which is electron deficient. This atom is referred to as the electrophilic center.

Thus, in photographic couplers as described, the timing group contains a nucleophilic group and an electrophilic group which are spatially related with respect to one another by a linking group (X) so that upon release from the coupler moiety the nucleophilic center and the electrophilic center will react to effect displacement of the inhibitor moiety from the timing group. The nucleophilic center should be prevented from reacting with the electrophilic center until release from the coupler moiety and the electrophilic center should be resistant to external attack, such as hydrolysis. Premature reaction can be prevented by attaching the coupler moiety to the timing group at the nucleophilic center or an atom in conjunction with a nucleophilic center, so that cleavage of the timing group and the inhibitor moiety from the coupler moiety unblocks the nucleophilic center and permits it to react with the electrophilic center, or by positioning the nucleophilic group and the electrophilic group so that they are prevented from coming into reactive proximity until release. The timing group can contain additional substituents, such as additional photographically useful groups (PUG), or precursors thereof, which may remain attached to the timing group or be released.

The PUG can be any group that is desirably made available in a photographic element in an imagewise fashion. The PUG can be a photographic dye or a photographic reagent.

It will be appreciated that in the timing group, for an intramolecular reaction to occur between the nucleophilic group and the electrophilic group, the groups should be spatially related after cleavage from the coupler, so that they can react with one another. Preferably, the nucleophilic group and the electrophilic group are spatially related within the timing group so that the intramolecular nucleophilic displacement reaction involves the formation of a 3- to 7-membered ring, most preferably a 5- or 6-membered ring.

It will be further appreciated that for an intramolecular reaction to occur in the aqueous alkaline environment encountered during photographic processing, displacing the timing group from the coupler moiety, the thermodynamics should be such and the groups be so selected that the free energy of ring closure plus the bond energy of the bond formed between the nucleophilic group and the electrophilic group is greater than the bond energy between the electrophilic group and other groups. Not all possible combinations of nucleophilic group, linking group, and electrophilic group will yield a thermodynamic relationship favorable to breaking of the bond between the electrophilic group and the inhibitor moiety. However, it is within the skill of the art to select appropriate combinations taking the above energy relationships into account.

A preferred class of timing group (T) is represented by the structure:

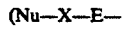

wherein:
Nu is a nucleophilic group attached to a position on COUP from which it will be displaced upon reaction of COUP with oxidized color developing agent;
E is an electrophilic group attached to an inhibitor moiety as described and is displaceable therefrom by Nu after Nu is displaced from COUP; and
X is a linking group for spatially relating Nu and E, upon displacement of Nu from COUP, to undergo an intramolecular nucleophilic displacement reaction with the formation of a 3- to 7-membered ring and thereby release INH—R$^1$.

Representative Nu groups contain electron rich oxygen, sulfur and nitrogen atoms. Representative E groups contain electron deficient carbonyl, thiocarbonyl, phosphonyl and thiophosphonyl moieties. Other useful Nu and E groups will be apparent to those skilled in the art.

In the following listings of representative Nu and E groups, the groups are oriented so that the lefthand bond of Nu is joined to COUP and the righthand bond of Nu is joined to X, while the lefthand bond of E is Joined to X and the righthand bond of E is joined to INH.

Representative Nu groups include:

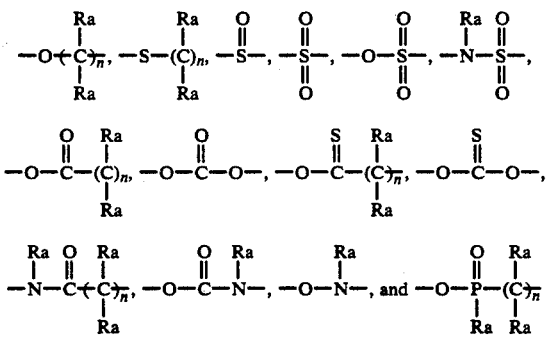

where each Ra is independently hydrogen, alkyl, such as alkyl of 1 to 20 carbon atoms including substituted alkyl such as methyl, ethyl, propyl, hexyl, decyl, pentadecyl, octadecyl, carboxyethyl, hydroxypropyl, sulfonamidobutyl and the like, or aryl, such as aryl of 6 to 20 carbon atoms including substituted aryl such as phenyl, naphthyl, benzyl, tolyl, t-butylphenyl, carboxyphenyl, chlorophenyl, hydroxyphenyl and the like, and n is an integer from 0 to 4 such that the ring formed by Nu, X and E upon nucleophilic attack of Nu upon the electrophilic center in E contains 3 to 7 ring atoms. Preferably Ra is hydrogen, alkyl of 1 to 4 carbon atoms or aryl of 6 to 10 carbon atoms.

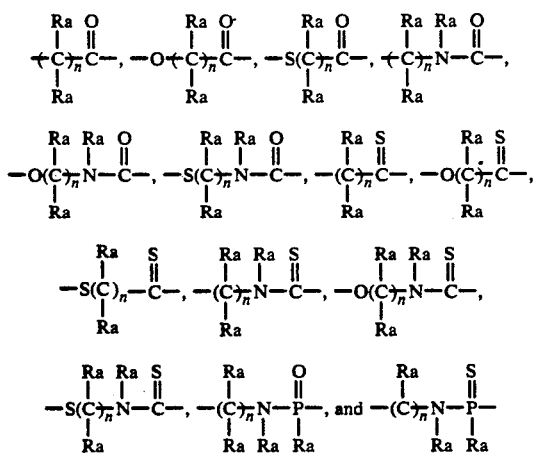

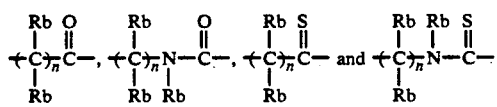

where Ra and n are defined above.

E is preferably an electrophilic group selected from the group consisting of

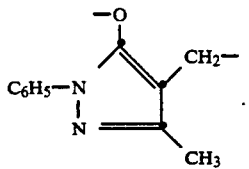

where each Rb is independently hydrogen, alkyl, such as alkyl containing 1 to 20 carbon atoms, preferably alkyl containing 1 to 4 carbon atoms, or aryl, such as aryl containing 6 to 20 carbon atoms, preferably aryl containing 6 to 10 carbon atoms; and n is 0 to 4, such that the ring formed upon reaction of the nucleophilic center in Nu with the electrophilic center in E contains 5- or 6-members.

The linking group represented by X can be an acyclic group such as alkylene, for example methylene, ethylene or propylene, or a cyclic group such as an aromatic group, such as phenylene or naphthylene, or a heterocyclic group, such as furan, thiophene, pyridine, quinoline or benzoxazine. Preferably X is alkylene or arylene. The groups Nu and E are attached to X to provide, upon release of Nu from COUP, favorable spatial relationship for nucleophilic attack of the nucleophilic center in Nu on the electrophilic center in E. When X is a cyclic group, Nu and E can be attached to the same or adjacent rings. Aromatic groups in which Nu and E are attached to adjacent ring positions are particularly preferred X groups.

X can be unsubstituted or substituted. The substituents can be those which will modify the rate of reaction, diffusion, or displacement, such as halogen, including fluoro, chloro, bromo, or iodo, nitro, alkyl of 1 to 20 carbon atoms, acyl, such as carboxy, carboxyalkyl, alkoxycarbonyl, alkoxycarbonamido, sulfoalkyl, alkylsulfonamido, and alkylsulfonyl, solubilizing groups, ballast groups and the like, or they can be substituents which are separately useful in the photographic element such as a stabilizer, an antifoggant, a dye (such as a filter dye, a solubilized masking dye) and the like. For example, solubilizing groups will increase the rate of diffusion; ballast groups will decrease the rate of diffusion; electron withdrawing groups will decrease the rate of displacement of the INH group.

Additionally, the timing group (T) can be any organic group which will serve to connect COUP to the inhibitor moiety and which, after cleavage from COUP, will cleave from the inhibitor moiety by an intramolecular elimination reaction, except that the timing group is not a pyrazolone group as exemplified by

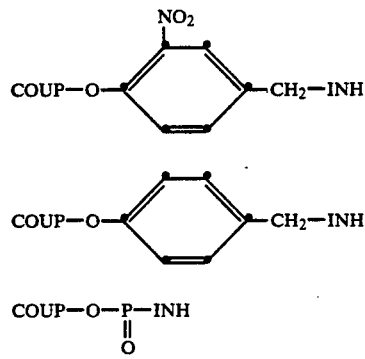

Such pyrazolone groups do not enable the preferred timing of release of the inhibitor moiety from the carrier moiety during photographic processing.

As used herein, the term "intramolecular elimination reaction" refers to a reaction in which a nucleophilic center of a compound reacts directly at another site on the compound, which is an electrophilic center, to effect elimination of a group or atom attached to the electrophilic center. Such compounds have a nucleophilic group and electrophilic group spatially related by the configuration of the molecule to promote elimination by electron transfer along a conjugated system. Such reactions are described, for example, in U.S. Pat. No. 4,409,323 and U.S. Pat. No. 4,564,587.

For convenience herein when the timing group (T) is of the type described in U.S. Pat. No. 4,409,323 the timing group can be described as a "quinone-methide timing group". Examples of useful couplers as described comprising a quinone-methide timing group are as follows:

COUP—O—[ring with NO2]—CH2—INH

COUP—O—[ring]—CH2—INH

COUP—O—P(=O)—INH

COUP—O—CH2—INH wherein COUP and INH are as described.

There follows a listing of patents and publications which describe representative useful COUP groups. Also listed are structures of preferred COUP, T, INH groups. In these structures Y represents, in the case of a dye forming coupler that is useful with couplers according to the invention, a hydrogen atom or a coupling-off group known in the photographic art. In the case of couplers according to the invention, Y represents Nu—X—E—INH, as described.

I. COUP's

A. Couplers which form cyan dyes upon reaction with oxidized color developing agents are described in such representative patents and publications as: U.S. Pat. Nos. 2,772,162, 2,895,826, 3,002,836, 3,034,892, 2,474,293, 2,423,730, 2,367,531, 3,041,236 and "Farbk-uppler-eine Literaturubersicht", published in Agfa Mitteilungen, Band III, pp. 156-175 (1961).

Preferably such couplers are phenols and naphthols which form cyan dyes on reaction with oxidized color developing agent and have the coupling-off group attached at the coupling position, that is the carbon atom in the 4-position. Structures of preferred such coupler moieties are:

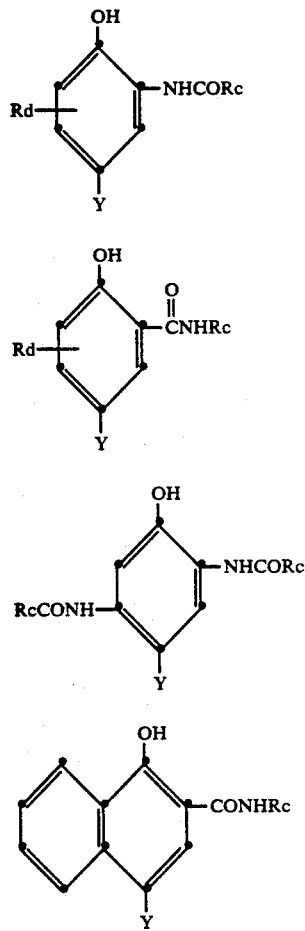

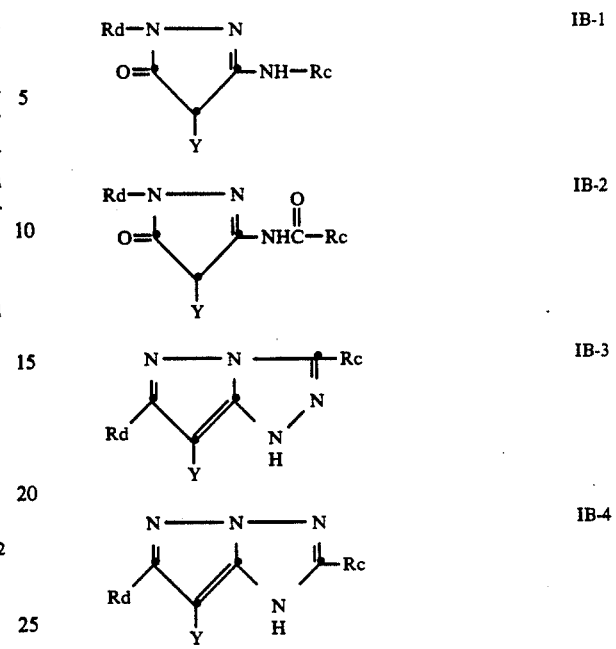

where Rc represents a ballast group, and Rd represents one or more halogen such as chloro or fluoro; alkyl containing 1 to 4 carbon atoms, such as methyl, ethyl or butyl, or alkoxy containing 1 to 4 carbon atoms, such as methoxy, ethoxy or butoxy groups.

B. Couplers which form magenta dyes upon reaction with oxidized color developing agent are described in such representative patents and publications as: U.S. Pat. Nos. 2,600,788, 2,369,489, 2,343,703, 2,311,082, 3,152,896, 3,519,429, 3,062,653, 2,908,573 and "Farbk-uppler-eine Literaturubersicht", published in Agfa Mitteilungen, Band III, pp. 126-156 (1961).

Preferably, such couplers are pyrazolones and pyrazolotriazoles which form magenta dyes upon reaction with oxidized color developing agents and have the Y attached to the coupling position. Structures of preferred such coupler moieties are:

where Rc and Rd are chosen independently to be a ballast group, unsubstituted or substituted alkyl, unsubstituted or substituted phenyl.

C. Couplers which form yellow dyes upon reaction with oxidized and color developing agent are described in such representative patents and publications as: U.S. Pat. Nos. 2,875,057, 2,407,210, 3,265,506, 2,298,443, 3,048,194, 3,447,928 and "Farbkuppler-eine Literaturubersicht", published in Agfa Mitteilungen, Band III, pp. 112-126 (1961).

Preferably such yellow-dye forming couplers are acylacetamides, such as benzoylacetanilides and have the Y group attached to the coupling position, that is the active methylene carbon atom.

Structures of preferred such coupler moieties are:

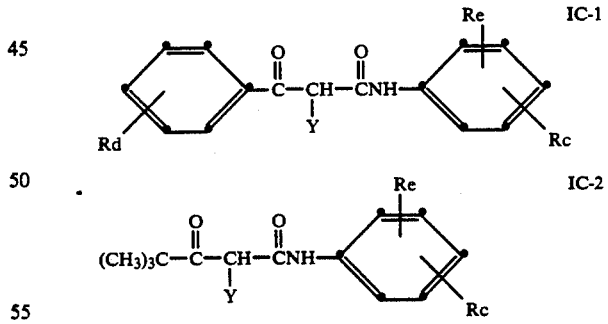

where Rc is as defined above and Rd and Re are hydrogen or one or more halogen, alkyl containing 1 to 4 carbon atoms, such as methyl and ethyl, or ballast groups, such as alkoxy of 16 to 20 carbon atoms.

D. Couplers which form colorless products upon reaction with oxidized color developing agent are described in such representative patents as: U.K. Patent No. 861,138; U.S. Pat. Nos. 3,632,345, 3,928,041, 3,958,993 and 3,961,959. Preferably such couplers are cyclic carbonyl containing compounds which form colorless products on reaction with oxidized color developing agent and have the Y group attached to the carbon atom in the α-position with respect to the carbonyl group.

Structures of preferred such coupler moieties are:

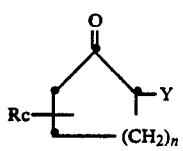
ID-1

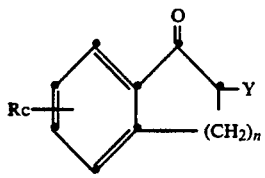
ID-2

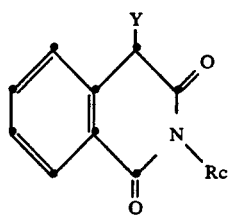
ID-3

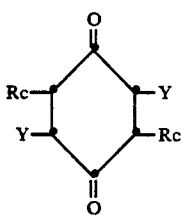
ID-4 where Rc is as defined above and n is 1 or 2.

E. Couplers which form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764.

Preferably such couplers are resorcinols or m-aminophenols which form black or neutral products on reaction with oxidized color developing agent and have the Y group para to a hydroxy group.

Structures of preferred such coupler moieties are:

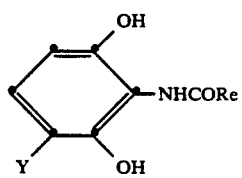
IE-1

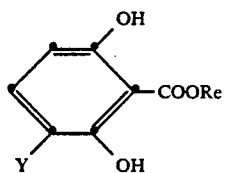
IE-2

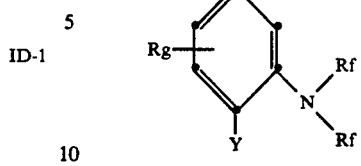
IE-3 where Re is alkyl of 3 to 20 carbon atoms, phenyl or phenyl substituted with hydroxy, halo, amino, alkyl of 1 to 20 carbon atoms or alkoxy of 1 to 20 carbon atoms; each Rf is independently hydrogen, alkyl of 1 to 20 carbon atoms, alkenyl of 1 to 20 carbon atoms, or aryl of 6 to 20 carbon atoms; and Rg is one or more halogen, alkyl of 1 to 20 carbon atoms, alkoxy of 1 to 20 carbon atoms or other monovalent organic groups.

II. Timing Groups

Examples of timing groups (T) are as follows:
A. Acyclic T groups:

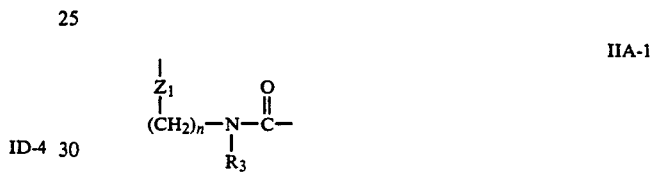
IIA-1 where n is 1–4, preferably 2 or 3, $Z_1$ is

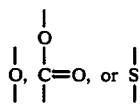

and $R_3$ is hydrogen, alkyl, such as alkyl of 1 to 20 carbon atoms, preferably alkyl of 1 to 4 carbon atoms, or aryl, such as aryl of 6 to 20 carbon atoms, preferably aryl of 6 to 10 carbon atoms.

B. Aromatic T groups:

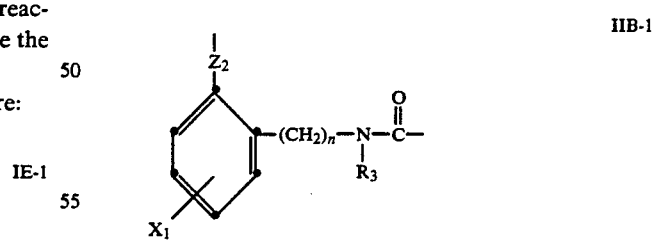
IIB-1

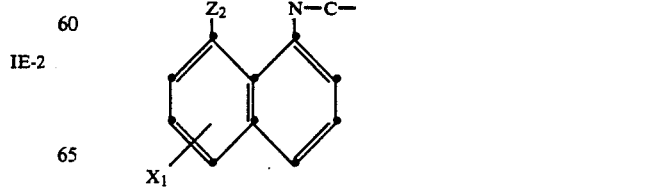
IIB-2 where n is 0 or 1; $Z_2$ is

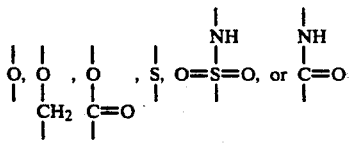

$R_3$ is as defined above; and $X_1$ is hydrogen or one or more substituent groups independently selected from cyano, fluoro, chloro, bromo, iodo, nitro, alkyl, such as alkyl of 1 to 20 carbon atoms, a dye, —$OR_4$, —$COOR_4$, —$CONHR_4$, —$NHCOR_4$, $NHSO_2R_4$, —$SO_2NHR_4$ of $SO_2R_4$, where $R_4$ is hydrogen, alkyl, such as alkyl of 1 to 20 carbon atoms, preferably alkyl of 1 to 4 carbon atoms, or aryl, such as aryl of 6 to 20 carbon atoms, preferably aryl of 6 to 10 carbon atoms.

C. Heterocyclic T groups:

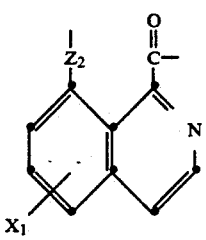

IIC-1

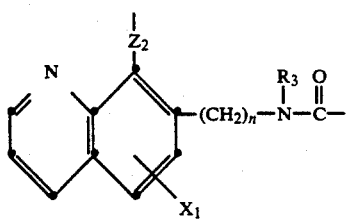

IIC-2

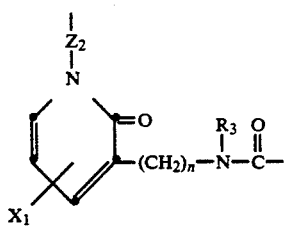

IIC-3 where n is 0 or 1, $Z_2$, $X_1$ and $R_3$ are as defined above.

D. Bis T groups:

IID-1

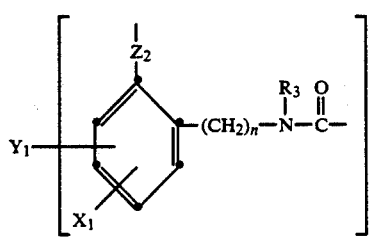

where $Y_1$ is a linking group, such as

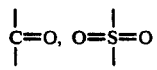

or —$NHSO_2CH_2SO_2NH$—; n is 0 or 1 and $X_1$, $Z_2$ and $R_3$ are as defined above.

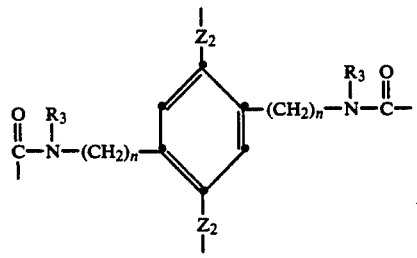

where n is 0 or 1 and $Z_2$, and $R_3$ are as defined above.

Such timing groups are described in, for example, U.S. Pat. No. 4,248,962.

E. Intramolecular elimination timing groups:

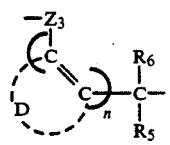

where $Z_3$ is a nucleophilic group such as N, O, S; n is 0, 1, 2, 3 or 4;

$R_5$ and $R_6$ are individually —H or substituted —C;

D represents the atoms required to form a carbocyclic or heterocyclic ring; except pyrazolone timing groups as exemplified by:

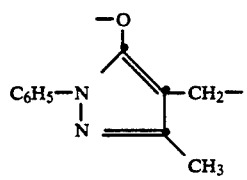

Such timing groups are described in, for example, U.S. Pat. No. 4,409,323 and U.S. Pat. No. 4,564,587.

Other illustrative timing groups are described in U.S. Pat. Nos. 4,684,604; 4,546,073; 4,618,571; 4,698,297; 4,737,451; and European Patent Application 255,085.

IV. INH Groups

A. INH groups that form development inhibitors upon release are described in such representative patents as U.S. Pat. Nos. 3,227,554; 3,384,657; 3,615,506; 3,617,291, 3,733,201, U.K. Pat. No. 1,450,479 and U.S. Pat. No. 4,477,563. Preferred development inhibitors are heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzotriazoles and benzodiazoles, triazoles and tetrazoles.

Typical examples of useful inhibitor groups (INH) are as follows: (In each of the structures, $R^1$ is as described, preferably t-butyl.)
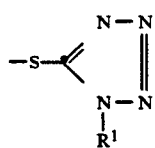
Specific examples are:
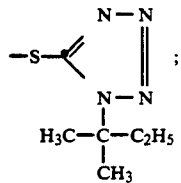
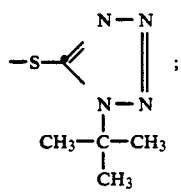
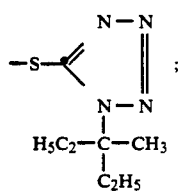
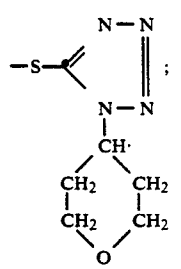
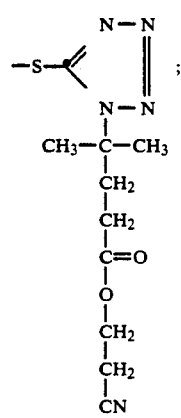
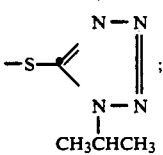
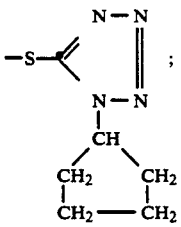
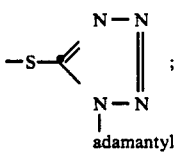
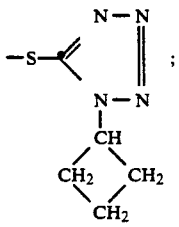
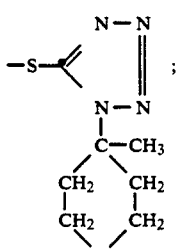
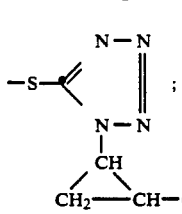
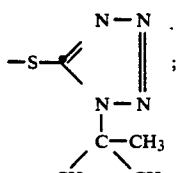
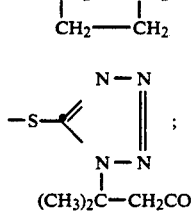

-continued
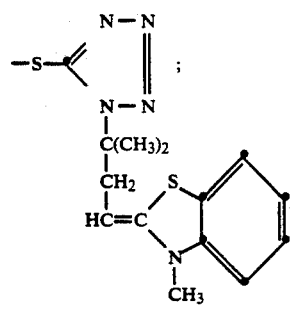
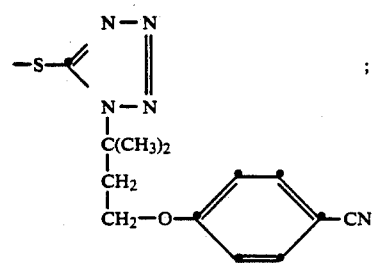
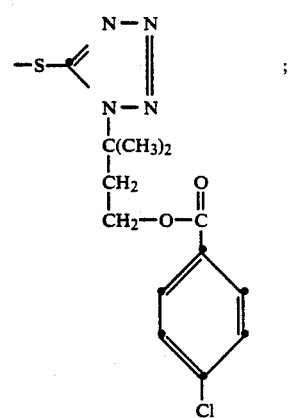
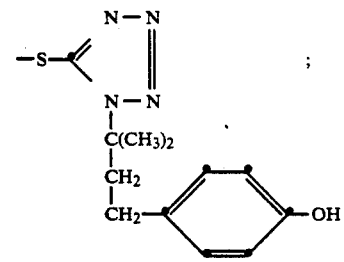
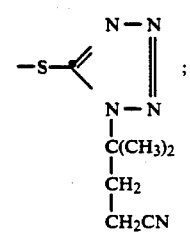
-continued
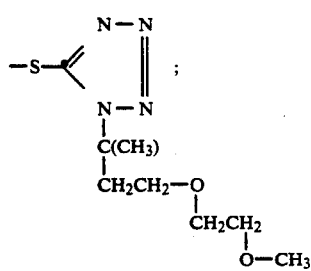
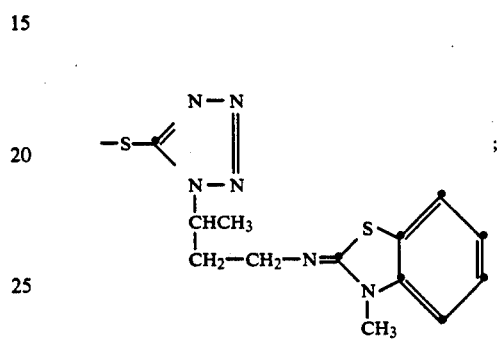
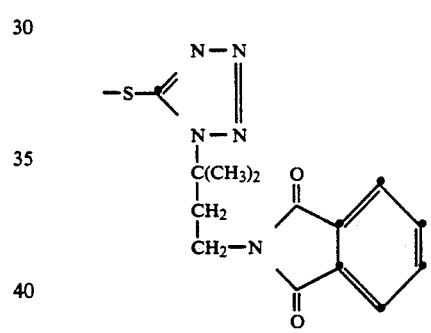
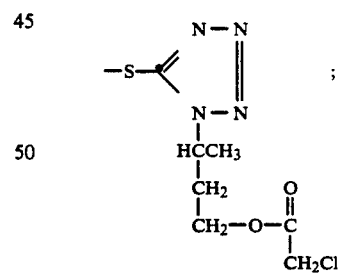
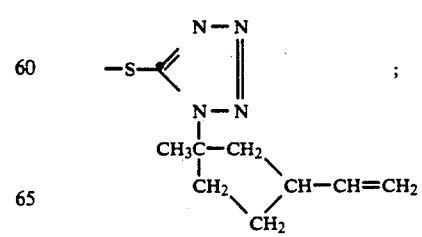

-continued
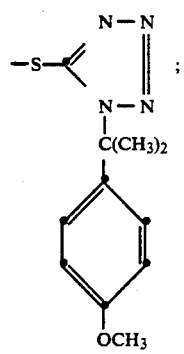
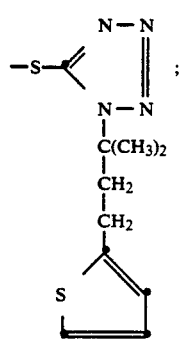
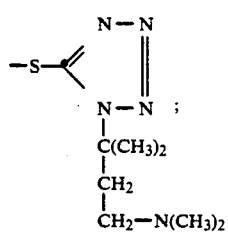
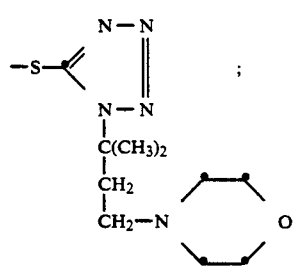
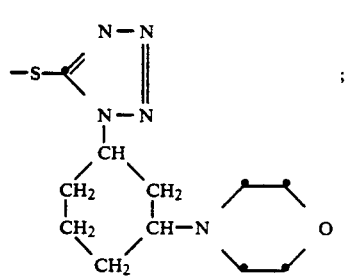
-continued
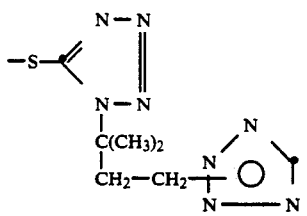
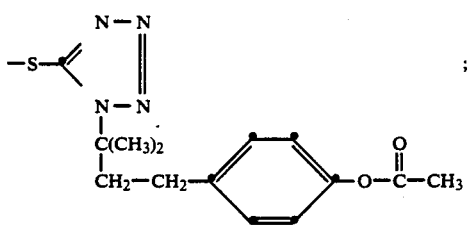
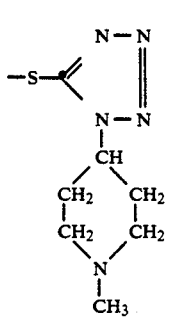
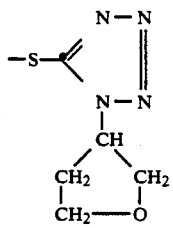
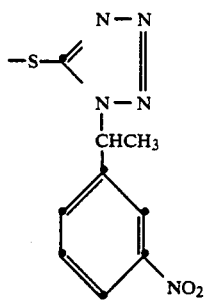
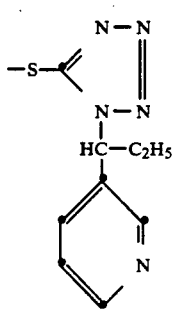

-continued
B) 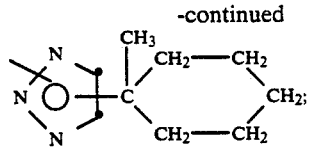
Specific examples are:
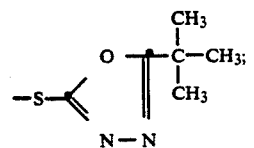
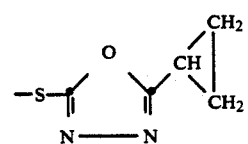
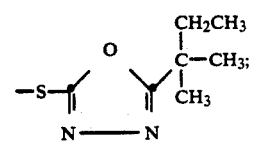
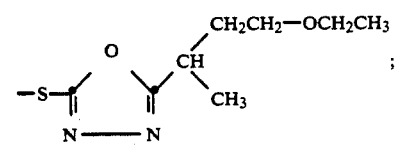
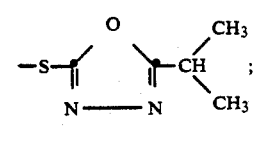
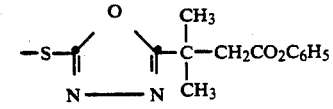
C) 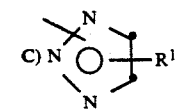
Specific examples are:
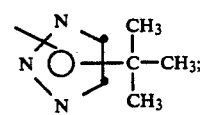
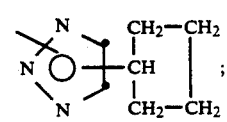
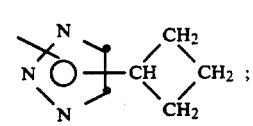
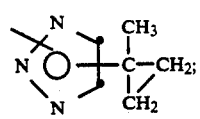
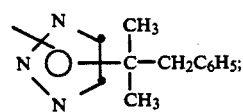
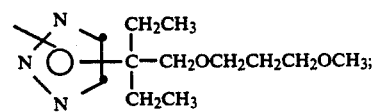
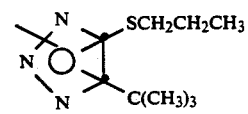
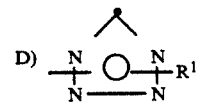
D) 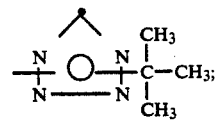
Specific examples are:
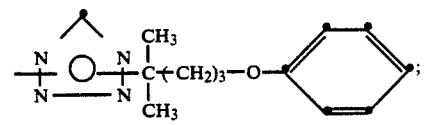
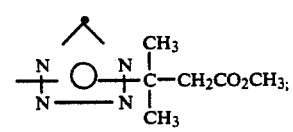
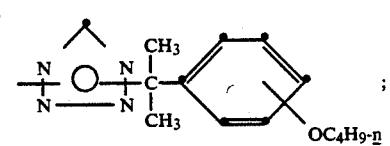
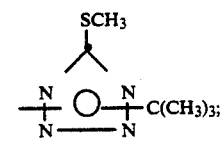
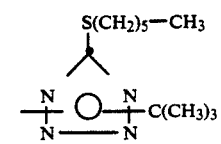

E) 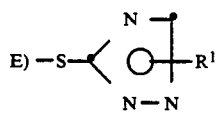
Specific examples are:
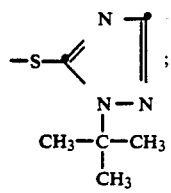
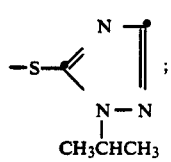
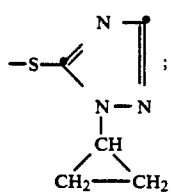
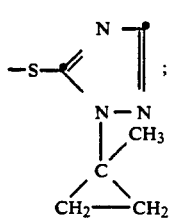
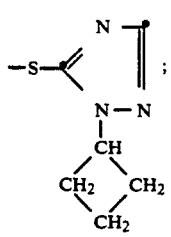
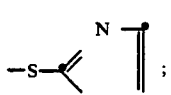
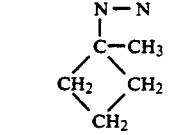
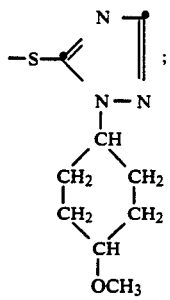
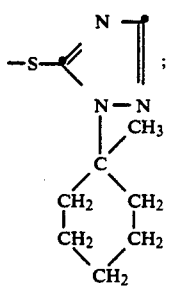
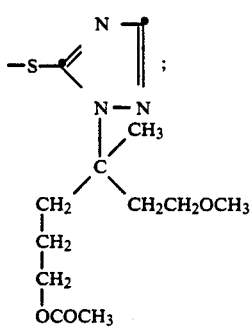
F) 
Specific examples are:
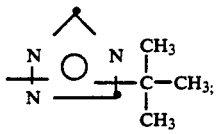
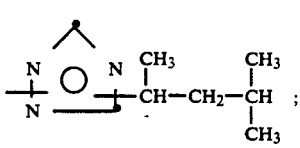
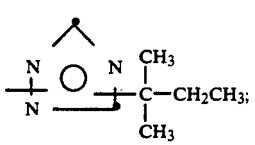

-continued
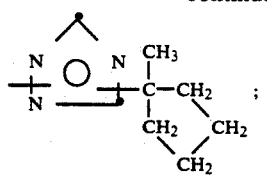
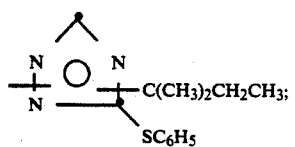
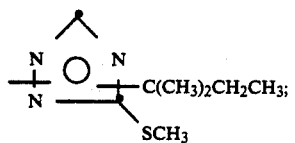
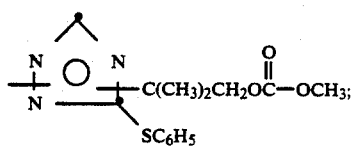
G) 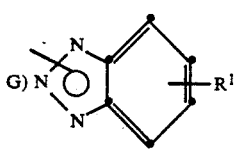
Specific examples are:
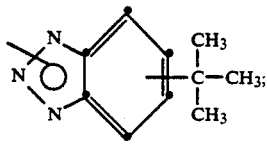
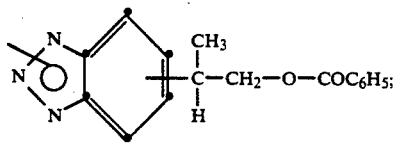
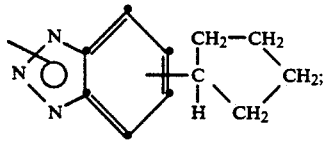
-continued
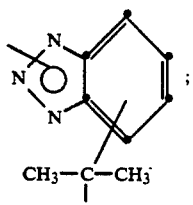
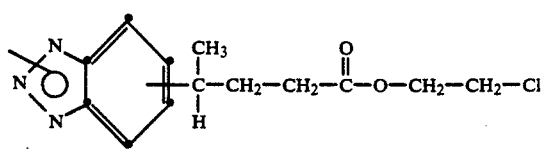
H) 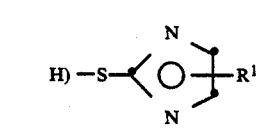
Specific examples are:
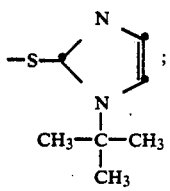
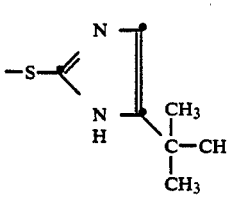
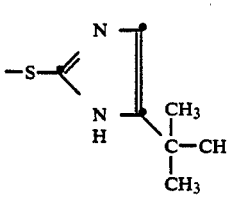
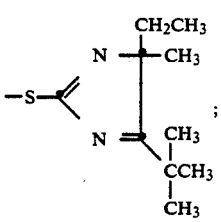
I) 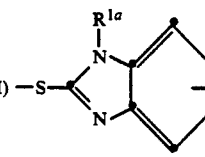
where R¹a is hydrogen or an unsubstituted or substituted hydrocarbon group, such as methyl, ethyl, propyl, n-butyl, t-butyl or phenyl.
Specific examples are:

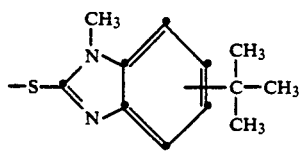
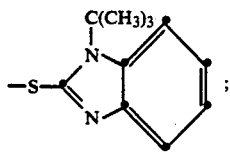
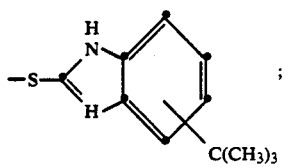
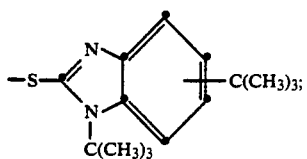
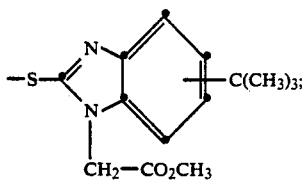
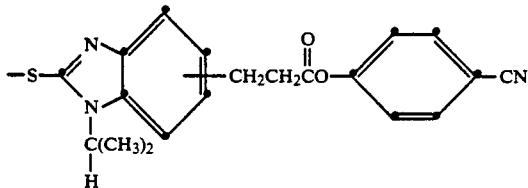
J) 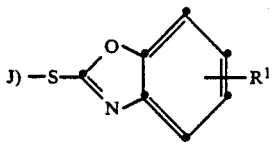
Specific examples are:
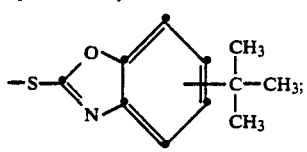
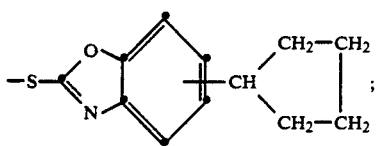

-continued
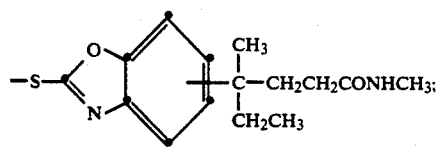
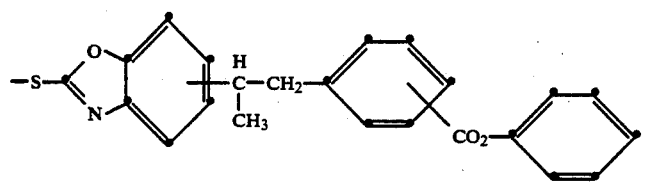
K) 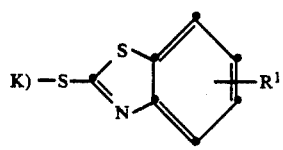
Specific examples are:
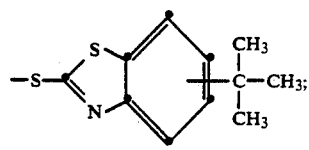
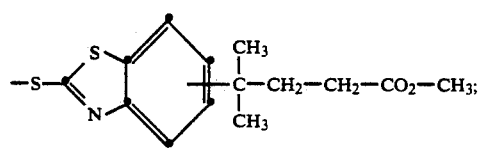
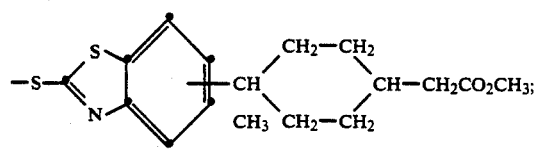
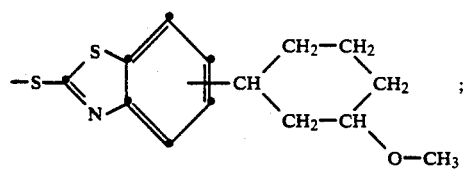
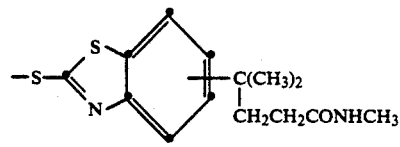
L) 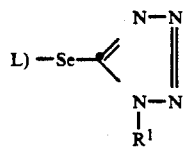
A Specific example is:

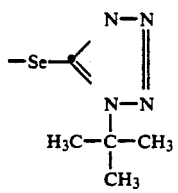
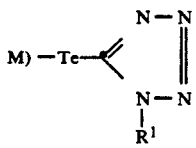
A Specific example is:
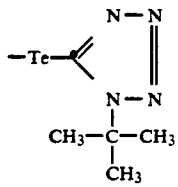
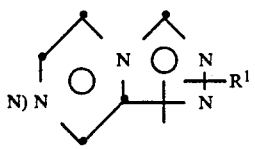
Specific examples are:
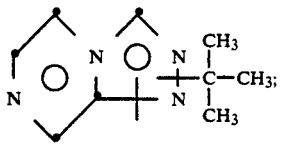
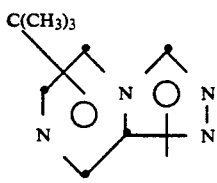
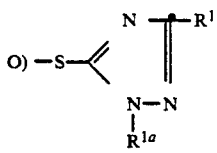
wherein $R^{1a}$ is hydrogen or an unsubstituted or substituted hydrocarbon group, such as methyl, ethyl, propyl, n-butyl, t-butyl or phenyl.
Specific examples are:
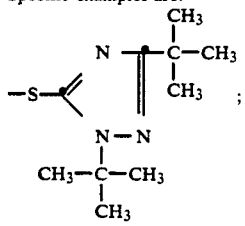
-continued
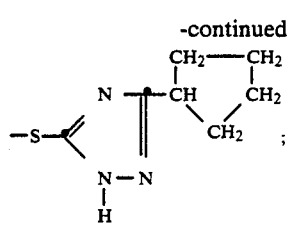

-continued

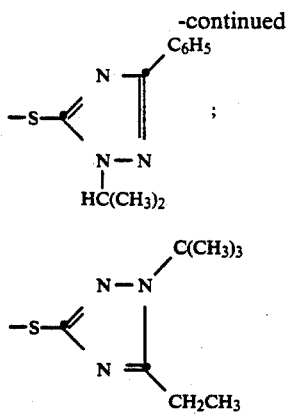

The inhibitor moiety can also be substituted with other groups that do not adversely affect the desired properties of compound (I). For example, the inhibitor moiety can contain substituent groups that are hydrolyzable, such as those described in U.S. Pat. No. 4,477,563.

The $R^1$ group on the inhibitor moiety can be any non-aromatic, sterically hindered substituent group that has (a) a tertiary carbon atom bonded directly to the inhibitor moiety or (b) a secondary carbon atom bonded directly to the inhibitor moiety and wherein the secondary carbon atom is not part of an unsubstituted carbocyclic ring containing at least 6 carbon atoms. The substituent $R^1$ is selected to provide increased acutance for an image formed upon exposure and processing of a photographic element containing compound (I) as described. The $R^1$ group is typically represented by the formula:

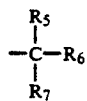

wherein at least two of $R_5$, $R_6$ and $R_7$ are unsubstituted or substituted hydrocarbon groups, such as alkyl containing 1 to 5 carbon atoms, for example, methyl, ethyl, propyl, and butyl. Preferably $R_5$, $R_6$ and $R_7$ are alkyl containing 1 to 4 carbon atoms.

The typical $R^1$ groups as described are:

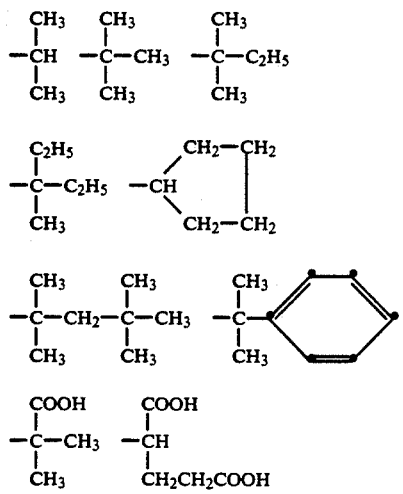

Preferred $R^1$ groups are t-butyl, isopropyl, cyclopentyl and t-amyl.

The timing group T and INH are selected and prepared to adjust to the activity of the adjoining carrier moiety, particularly a coupler moiety and the other groups of the coupler in order to optimize release of the INH for its intended purpose. Accordingly, INH groups of differing structural types are useful which enable timing groups having a range of activities. Various properties, such as pKa, are also usefully considered in optimizing the selection of optimum groups for a particular purpose. An example of such a selection could involve, for instance, a benzotriazole moiety as an inhibitor. Such a benzotriazole moiety can be released too quickly for some intended purposes from a timing group which involves an intramolecular nucleophilic displacement mechanism; however, the benzotriazole moiety can be modified as appropriate by substituent groups that change the rate of release.

The photographic compound (I) as described can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements as described can be processed by conventional techniques in which color forming couplers and color developing agents are incorporated in separate processing solutions or compositions or in the element.

Photographic elements in which the compound (I) is incorporated can be a simple element comprising a support and a single silver halide emulsion layer or they can be multilayer, multicolor elements. The compound (I) can be incorporated in at least one of the silver halide emulsion layers and/or in at least one other layer, such as an adjacent layer, where it will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element as described can comprise a support having thereon a red-sensitive silver halide emulsion unit having associated therewith a cyan dye image providing material, a green-sensitive silver halide emulsion unit having associated therewith a magenta dye image providing material and a blue-sensitive silver halide emulsion unit having associated therewith a yellow dye image-providing material, at least one of the silver halide emulsion units having associated therewith a photographic coupler as described. Each silver halide emulsion unit can be composed of one or more layers and the various units and layers can be arranged in different locations with respect to one another. units of of the photographic element. If COUP, T and/or INH are diffusible moieties, the layer or unit affected by INH can be controlled by incorporating in appropriate locations in the element a scavenger layer which will confine the action of COUP, T and/or INH to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure,* Jan. 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The photographic couplers can be used in photographic elements in the same way as photographic couplers which release inhibitors have previously been used in photographic elements.

Depending upon the nature of the particular INH, the couplers can be incorporated in a photographic element for different purposes and in different locations.

The coupler can be employed in a photographic element like couplers which release development inhibitors have been used in the photographic art. Couplers as described can be contained in, or in reactive association with, one or more of the silver halide emulsion units in a color photographic element. If the silver halide emulsion unit is composed of more than one layer, one or more of such layers can contain the coupler as described. The layers can contain other photographic couplers conventionally used in the art. The coupling reaction using couplers as described can form dyes of the same color as the color forming coupler(s) in the layer or unit, it can form a dye of a different color, or it can result in a colorless or neutral reaction product. The range of operation between layers of the development inhibitor released from the coupler as described can be controlled by the use of scavenger layers, such as a layer of fine grain silver halide emulsion. Scavenger layers can be in various locations in an element containing couplers as described. They can be located between layers, between the layers and the support, or over all of the layers.

Compounds as described can be prepared by methods known in the organic compound synthesis art. Typically, the couplers of this invention are prepared by first attaching the timing group to the appropriate coupler moiety, or a derivative of the coupler moiety. The product is then reacted with an appropriate derivative of the inhibitor to form the desired coupler. Known reactions are employed to perform these steps. The following examples illustrate the way in which these steps can be performed using specific reactants and reactions.

The following compounds illustrate methods of preparing compounds according to the invention.

EXAMPLE 1

Preparation of 1-Tert-butyl-2-tetrazoline-5-thione (Ia)

Combined solutions of 50.0 g (0.435 mol) tert-butyl isothiocyanate in 125 ml ethanol and 56.6 g (0.850 mol) sodium azide in 900 ml water were heated under reflux with stirring for 5.5 hours. After cooling, the solution was acidified to pH 1 with hydrochloric acid and extracted with ether. The extracts were washed with water and aqueous saturated sodium chloride solution, dried over magnesium sulfate, and evaporated to yield 21 g of colorless oil which later crystallized. The product of a repeat of this preparation was triturated with ligroine to yield colorless crystals of Ia mp 92°–94°, confirmed by NMR, infrared, and mass spectral data as well as elemental analysis.

EXAMPLE 2

Preparation of Coupler 17

A solution of 3.9 g (0.025 mol) Ia and 18.7 g (0.025 mol) II in 140 ml pyridine was stirred at room temperature overnight under nitrogen then poured into 1 liter ice water containing 140 ml concentrated hydrochloric acid. The organic phase was dissolved in ethyl acetate and washed successively with saturated sodium bicarbonate solution, water, and saturated sodium chloride solution, then dried over magnesium sulfate and concentrated. The resultant oil was purified by silica gel chromatography and crystallized from hexane/ethyl acetate to yield 3.0 g Coupler 17, mp 107°–108° C., with the correct elemental analysis.

EXAMPLE 3

Preparation of Coupler 19

1-Isopropyl-2-tetrazoline-5-thione, prepared from isopropyl isothiocyanate by a procedure analogous to that of Example 1, was combined with II at the same molar levels as in the procedure of Example 2 to yield 5.6 g Coupler 19, mp 121°–122° C. with the correct analysis.

EXAMPLE 4

Preparation of Coupler 18

1-Cyclopentyl-2-tetrazoline-5-thione, prepared from cyclopentyl isothiocyanate by the procedure of Example 1, was combined with II at the same molar levels as in Example 2 to yield 4.0 g, Coupler 18, mp 98°–105° C. with the correct elemental analysis.

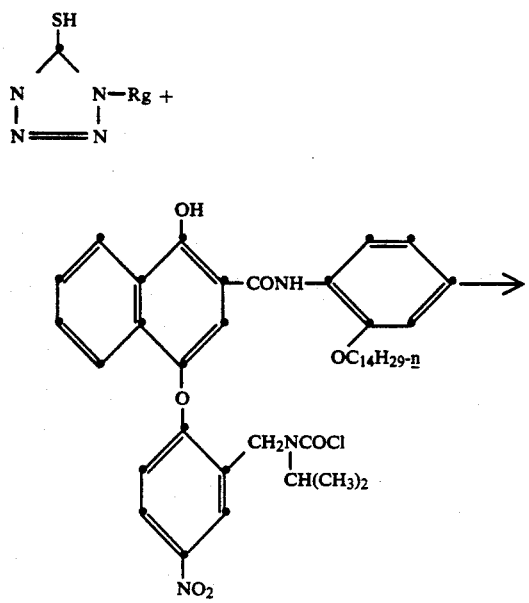

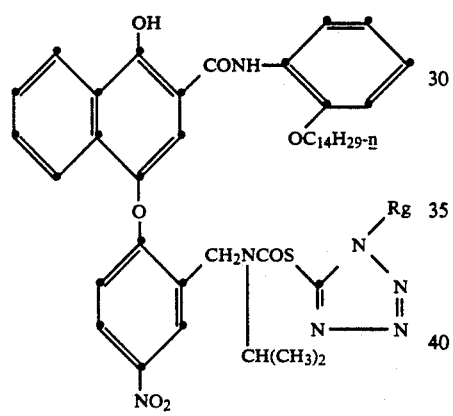

Ia, Rg = —C(CH₃)₃    Coupler 17, R = —C(CH₃)₃
Ib, Rg = —CH(CH₃)₂    Coupler 19, R = —CH(CH₃)₂
Ic, Rg = —[S]    Coupler 18, R = —[S]

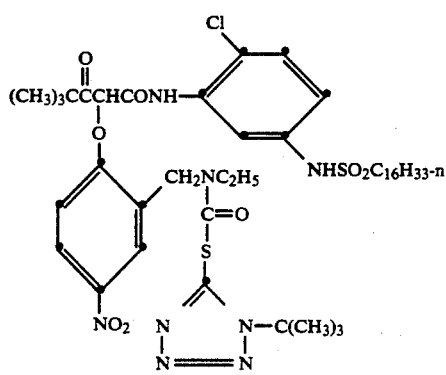

EXAMPLE 5

Preparation of Coupler 32

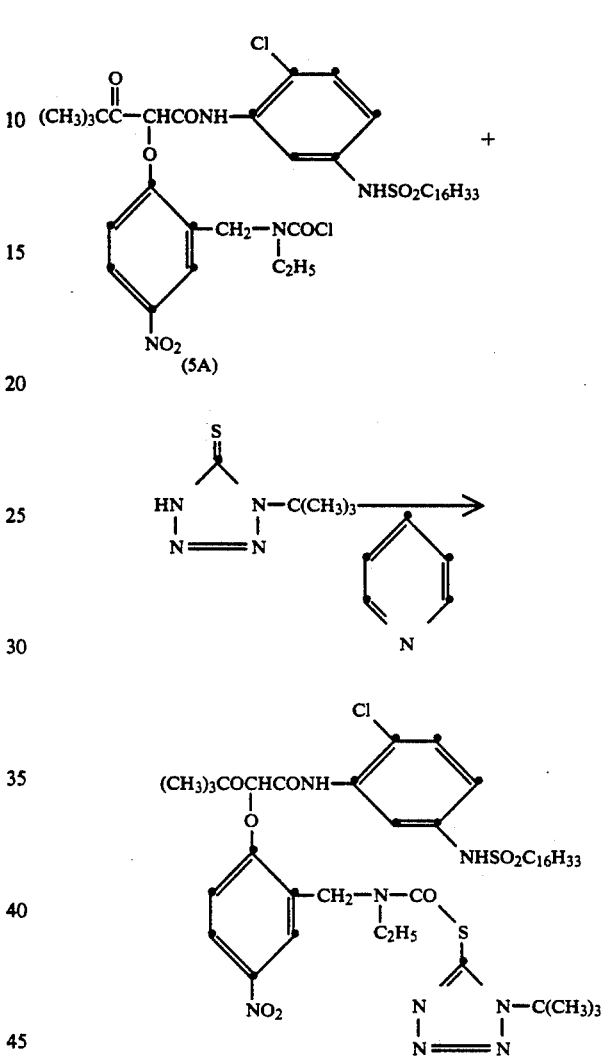

A solution of carbamoyl chloride 5A (36 g, 0.044 mole) and t-butyl mercapto-tetrazole (5.7 g, 0.047 mole) in 340 ml pyridine was stirred at room temperature for eighteen hours. The reaction mixture was poured into 1.5 liter ice-water mixture containing 470 ml concentrated hydrochloric acid and extracted with ethyl acetate. The combined extracts were washed with brine, dried over magnesium sulfate, filtered and concentrated in vacuo to an oil which was chromatographed over silica (ethyl acetatecyclohexane). The product containing fractions were combined and evaporated in vacuo to yield 23.9 g of an off white gun.

The elemental analysis was:
Calculated C 56.5; H 7.2; N 12.0; Cl 3.8; S 6.9
Found: C 56.7; H 7.2; N 11.9; Cl 3.8; S 6.1

EXAMPLE 6

Preparation of Compound 1

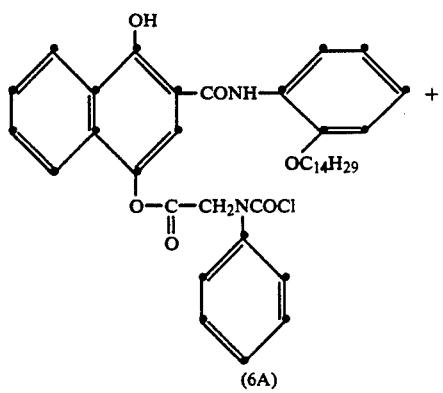
(6A)

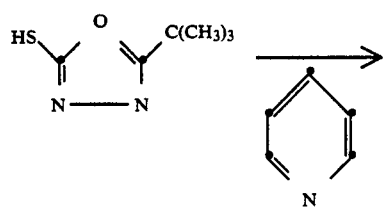

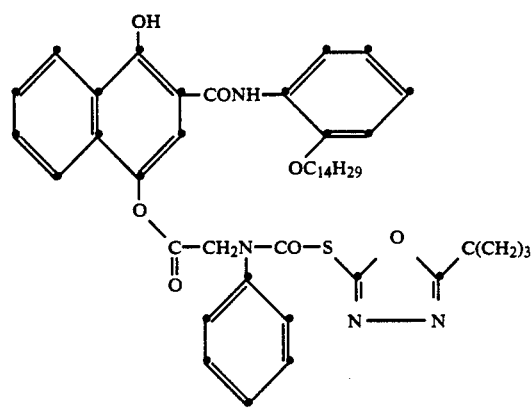
Coupler 1

A solution of the carbamoyl chloride 6A (6.6 g, 0.0096 mole) and t-butyl mercapto-oxadiazole (1.51 g, 0.0096 mole) in 50 ml pyridine was stirred for three hours at room temperature. The solvent was removed in vacuo. The residue chromatographed over silica (ethyl acetate-hexane), and the product containing fractions combined and evaporated to yield an oil which was crystallized from hexane-ethyl acetate to yield 2.6 g of a cream colored solid, m.p.

The elemental analysis was:

Calculated: C 68.3; H 7.0; N 6.9; S 4.0

Found: C 68.4; H 6.8; N 6.6; S 4.1

EXAMPLE 7

Preparation of 4

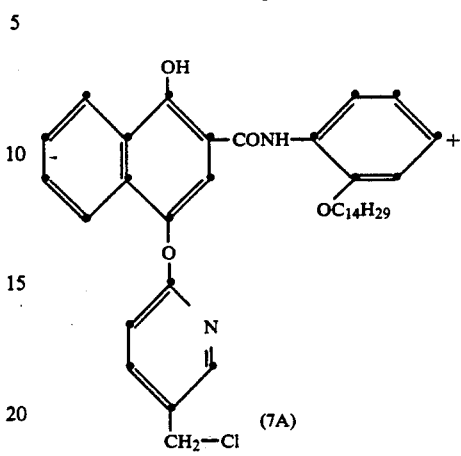
(7A)

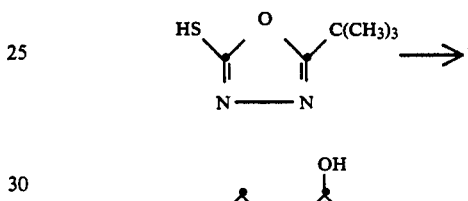

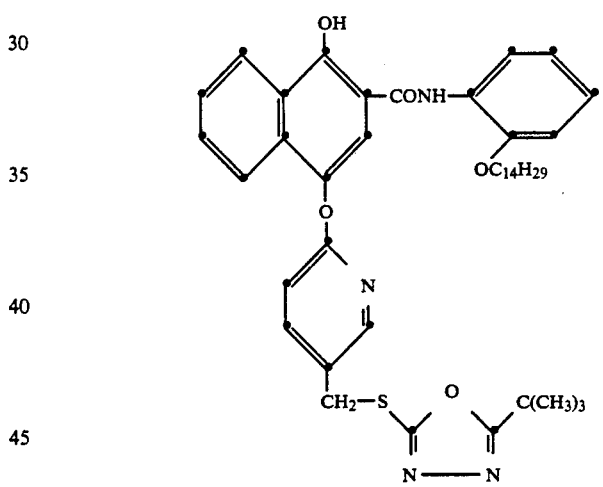

A mixture of 4.8 g (8 mmole) of the benzyl chloride 7A, 1.58 g (10 mmole) of t-butyl mercaptooxadiazole, 0.84 g (10 mmole) sodium bicarbonate, and 0.05 g tetrabutylammonium bromide in 50 ml dichloromethane and 30 ml water was stirred at room temperature for 18 hours. The organic layer was separated, dried over magnesium sulfate, filtered, and concentrated in vacuo to yield an oil which was crystallized from acetic acid to yield 3.75 g of the desired product, m.p. 93°-4° C.

The elemental analysis was:

Calculated: C 69.9; H 7.4; N 7.7; S 4.3

Found: C 69.5; H 7.5; N 7.4; S 4.3

The following examples further illustrate the invention. The following compounds can be prepared using procedures similar to those described:

1. 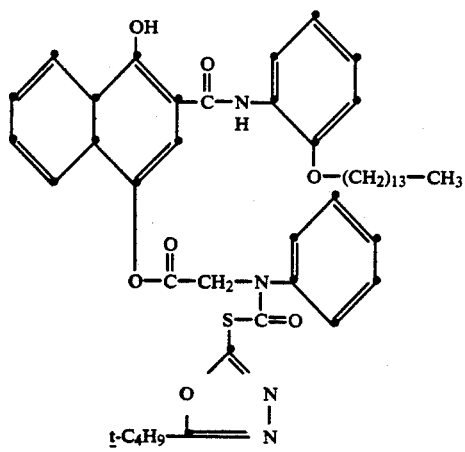
2. 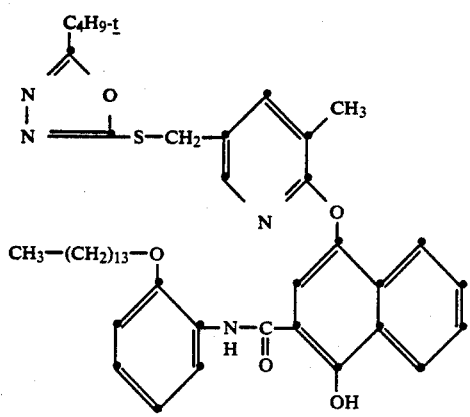
3. 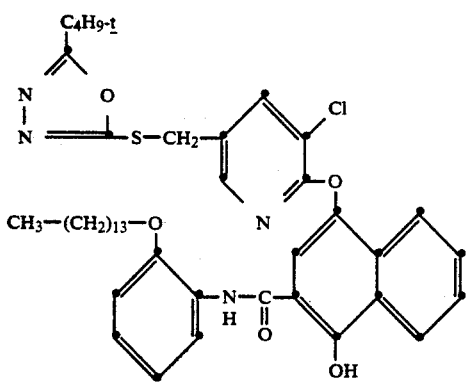
4. 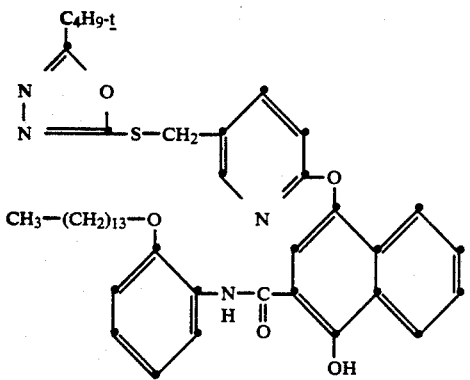

5.
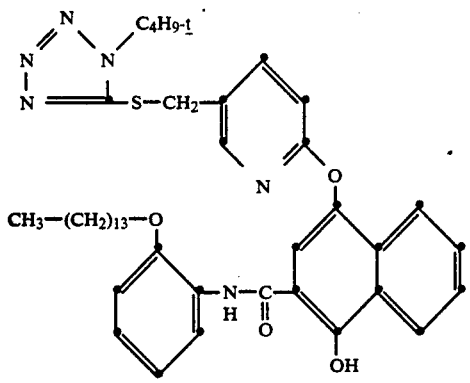
6.
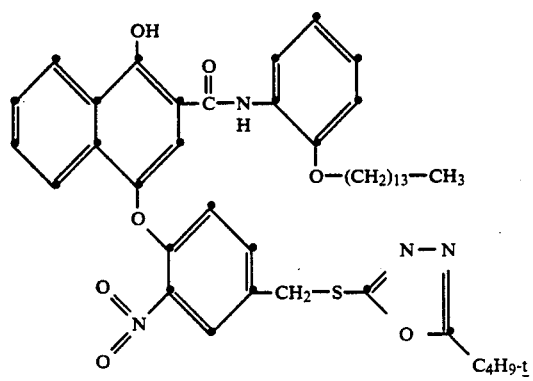
7.
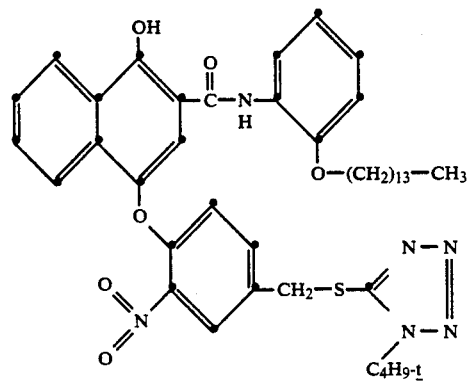
8.
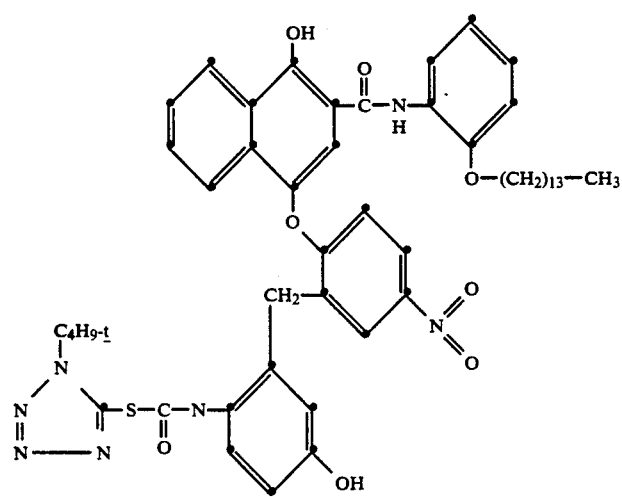

9.
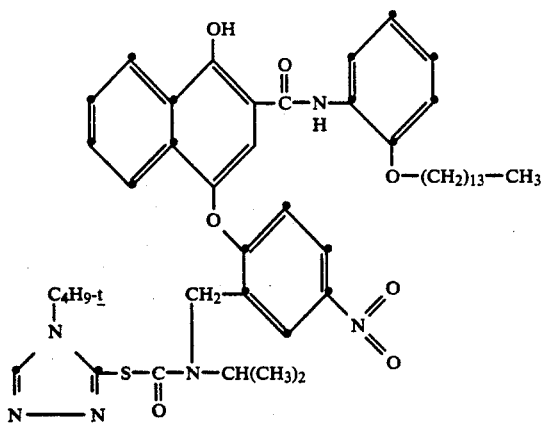
10.
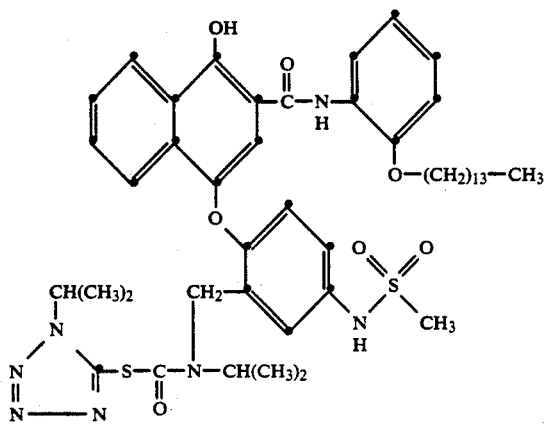
11.
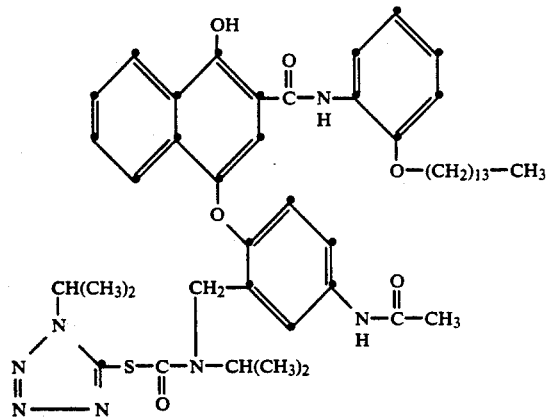
12.
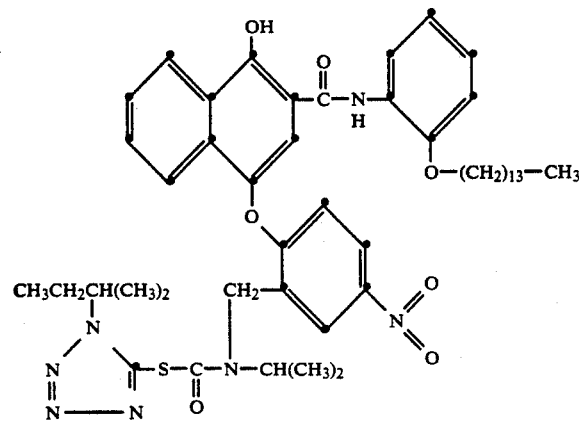

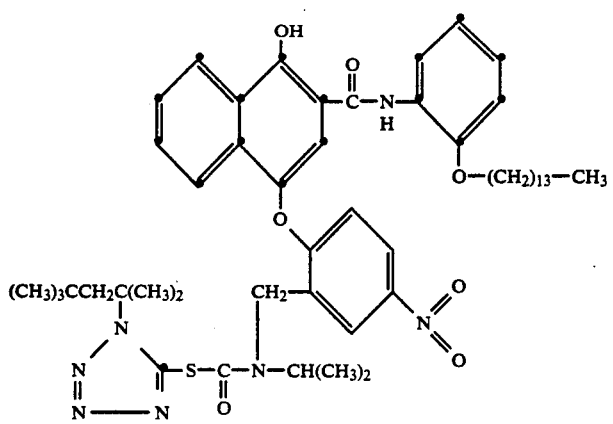
13.
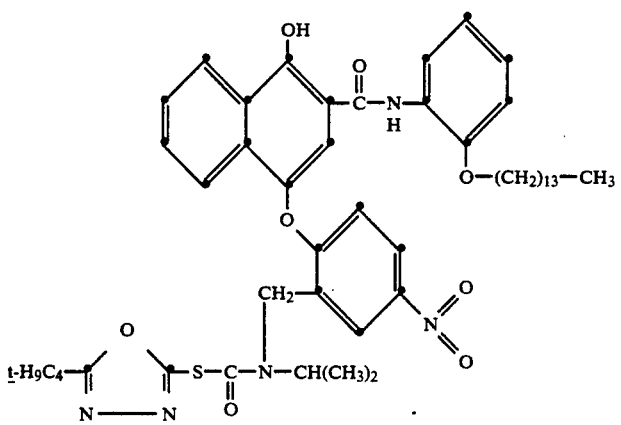
14.
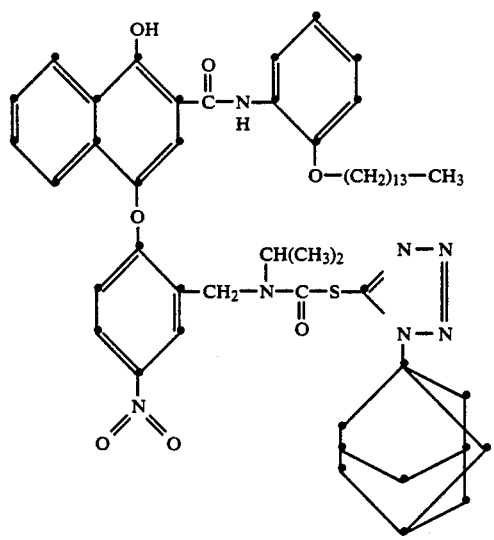
15.

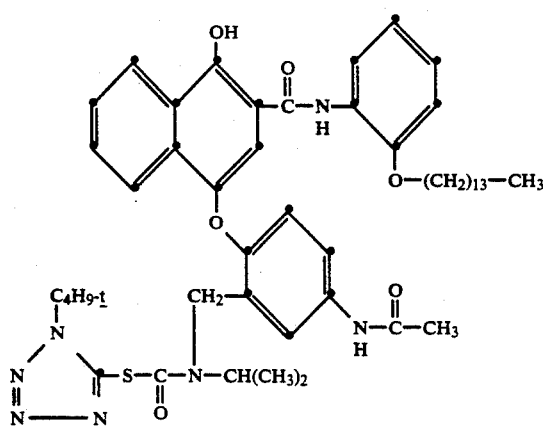
16.
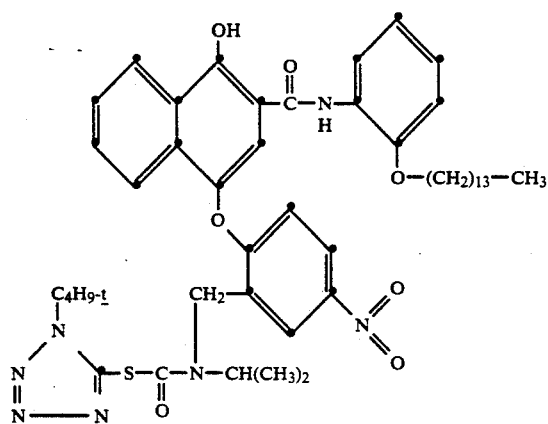
17.
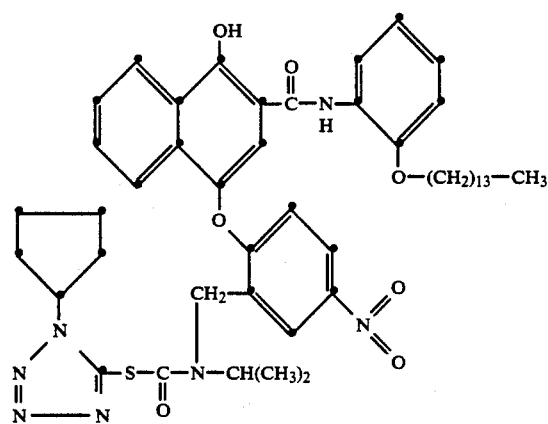
18.

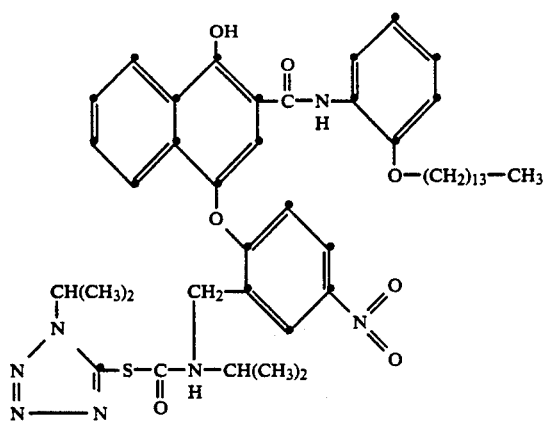
19.
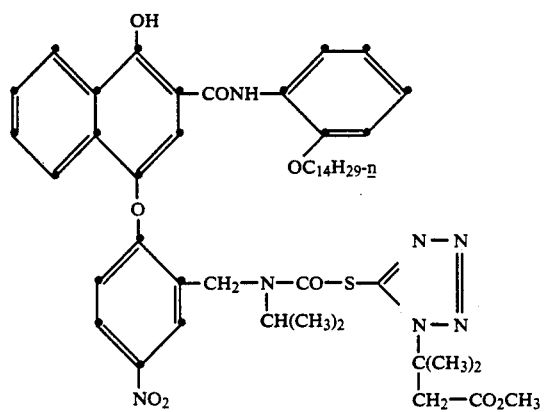
20.
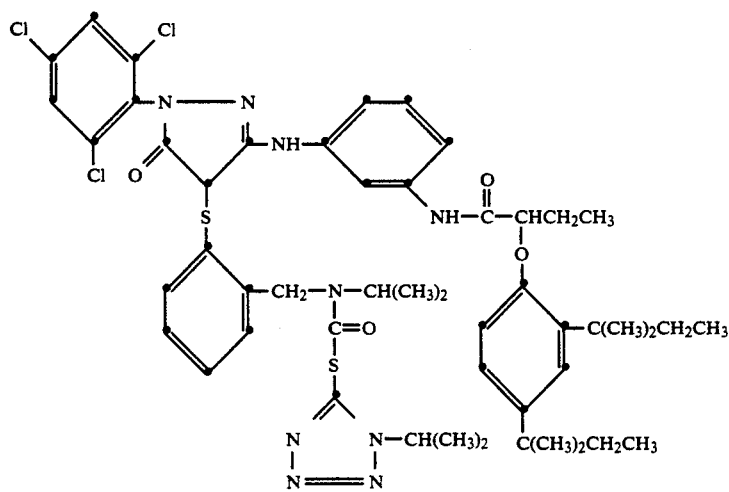
21.

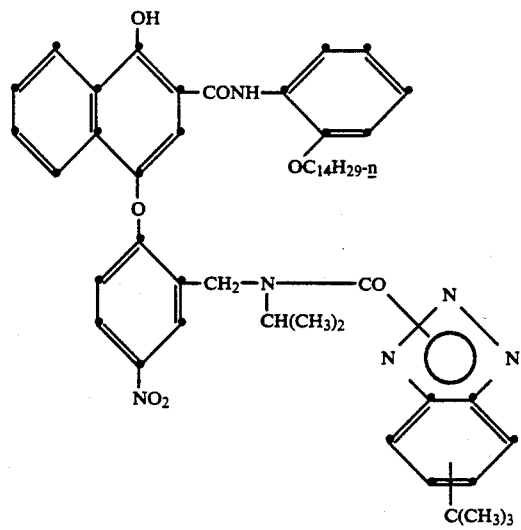
22.
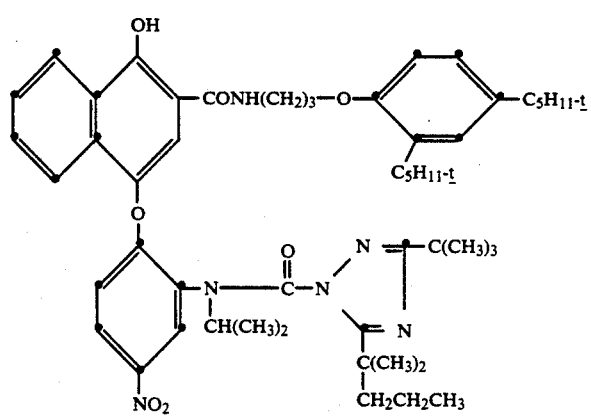
23.
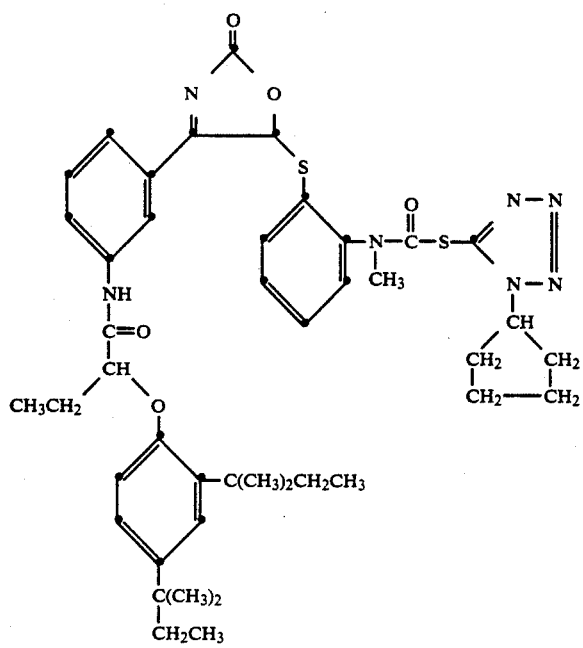
24.

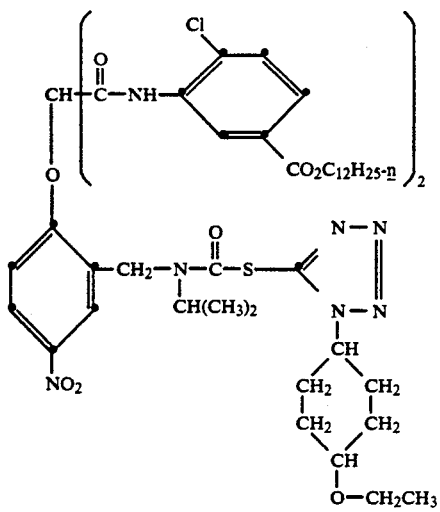
25.
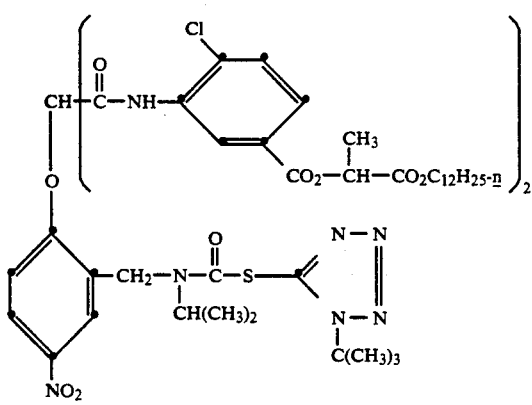
26.
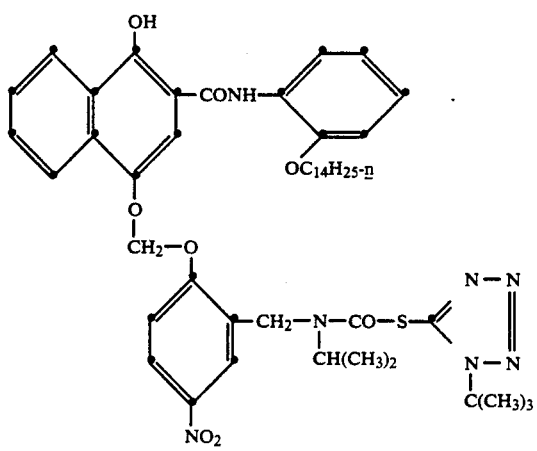
27.

28.
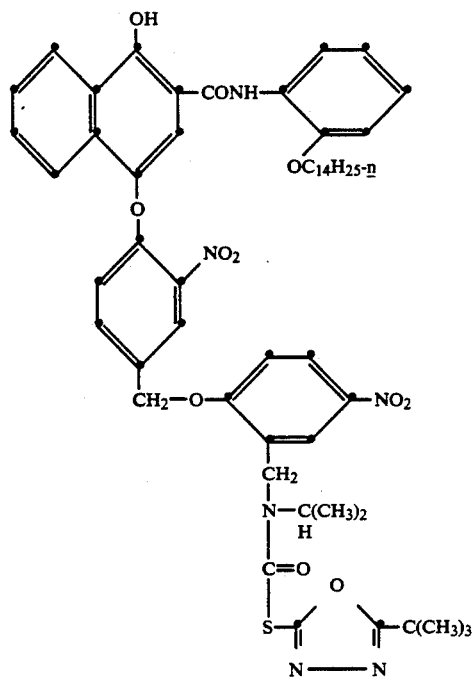
29.
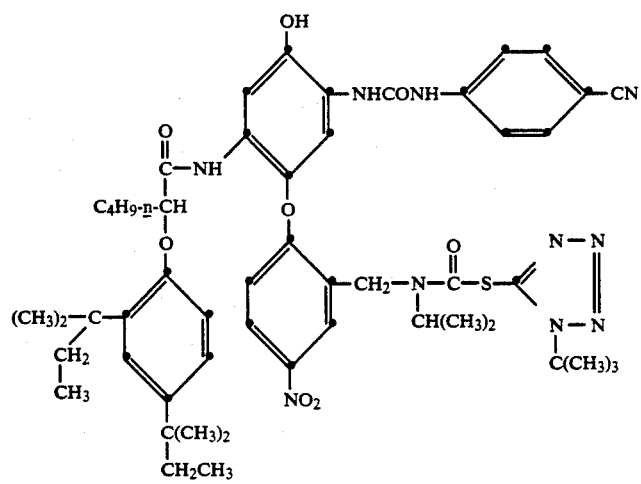
30.
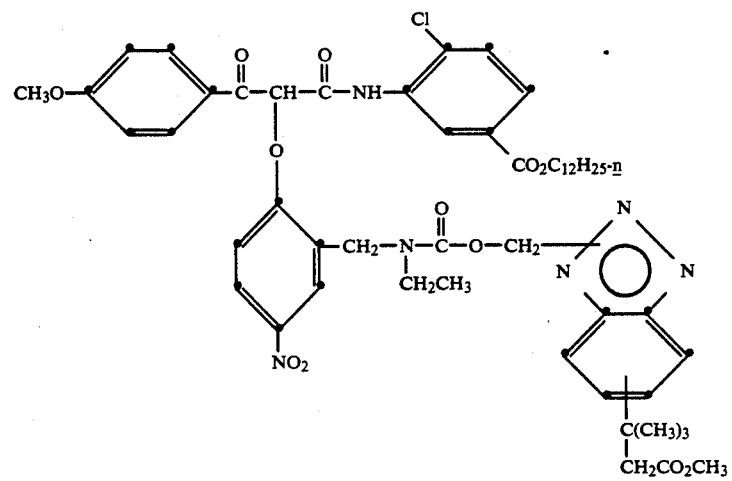

-continued
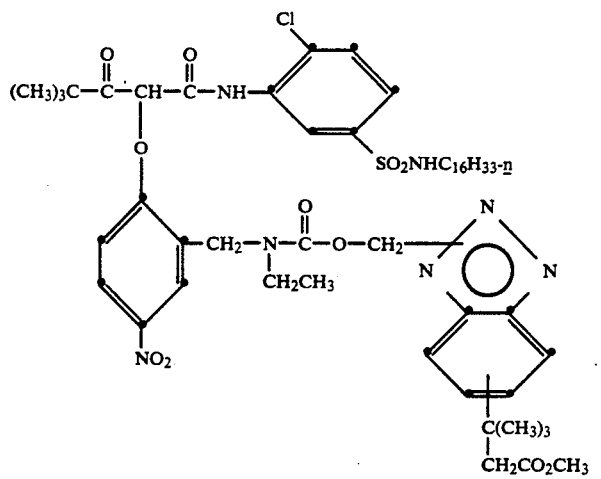
31.
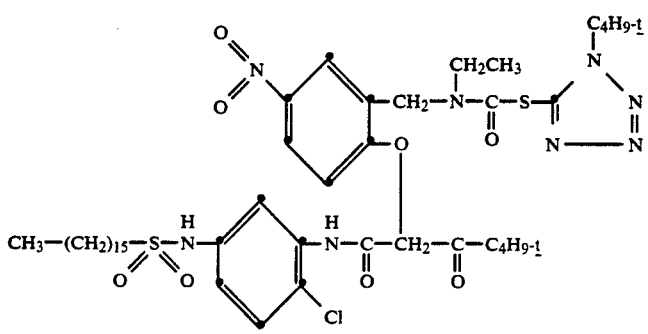
32.
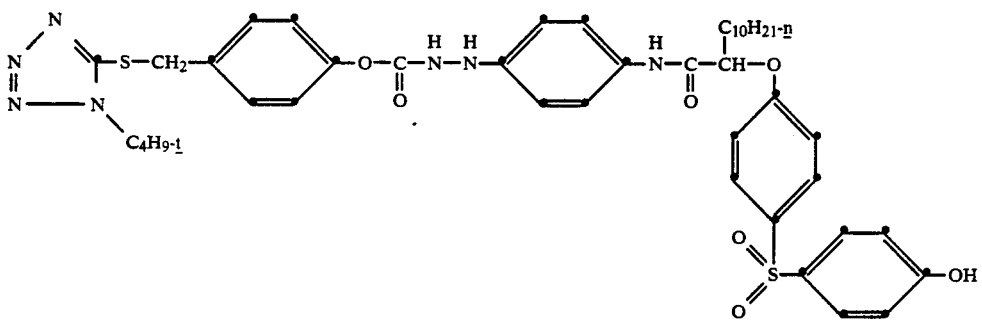
33.
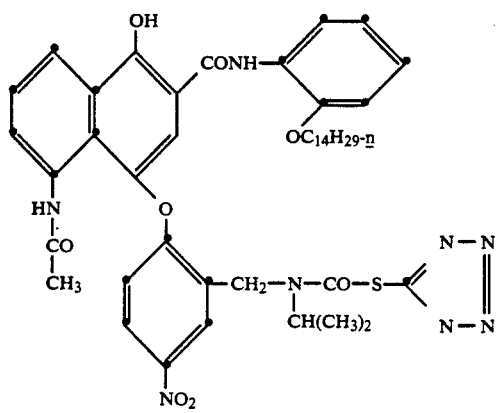
34.

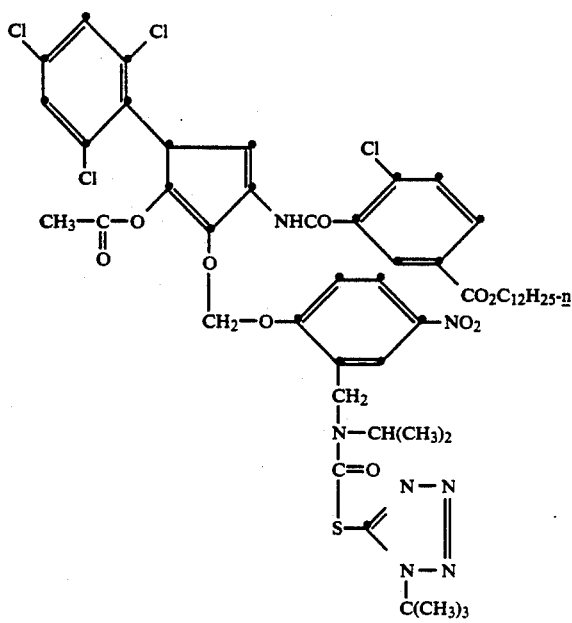
35.
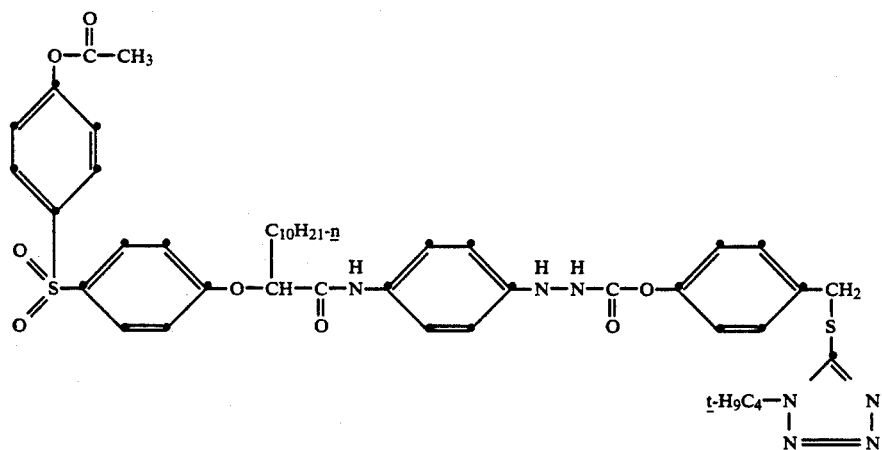
36.
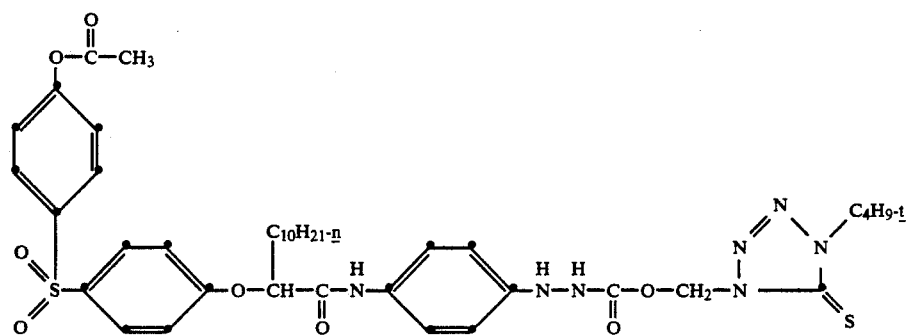
37.

-continued
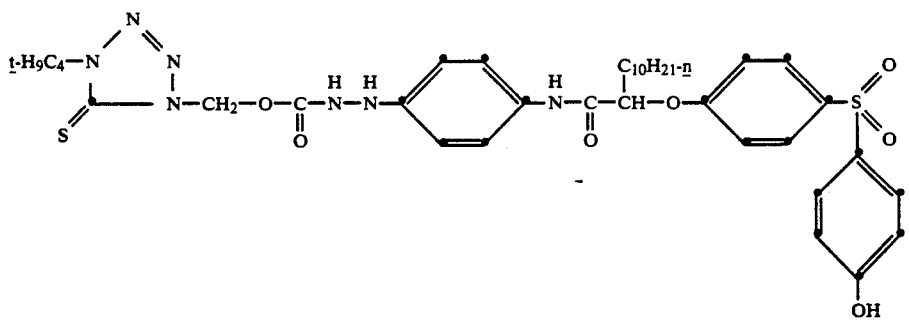 38.
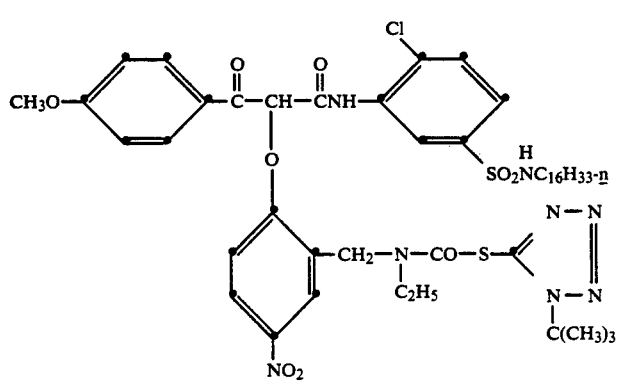 39.
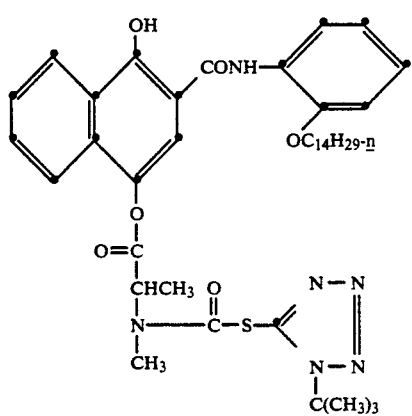 40.
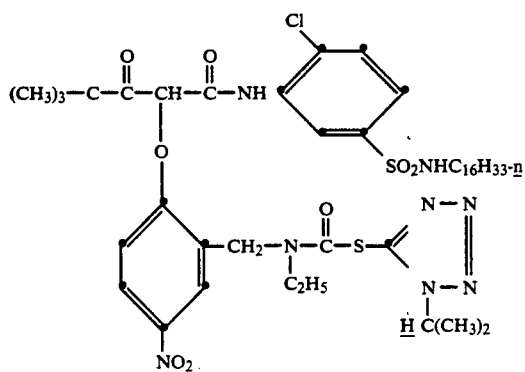 41.

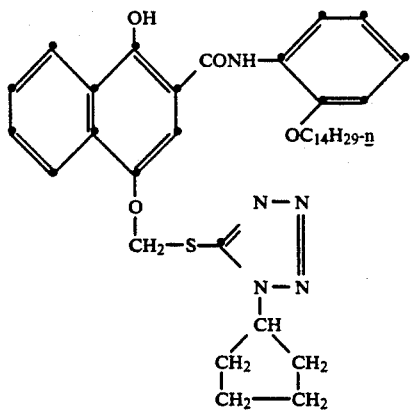
42.
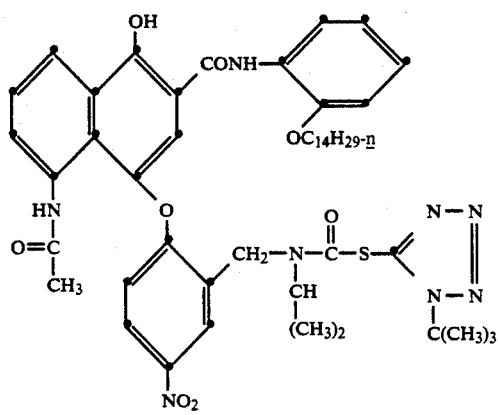
43.
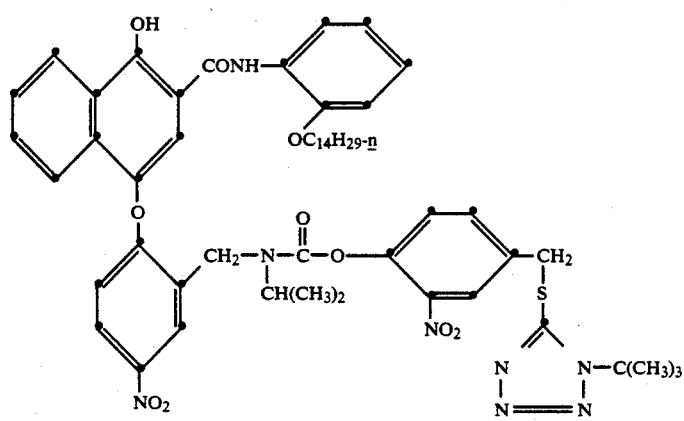
44.
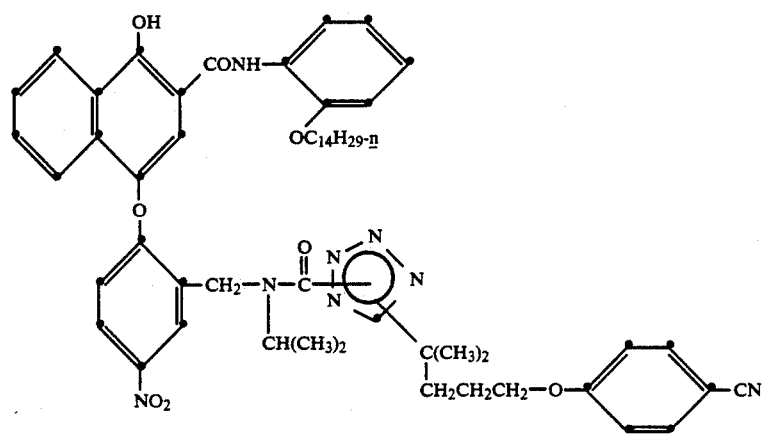
45.

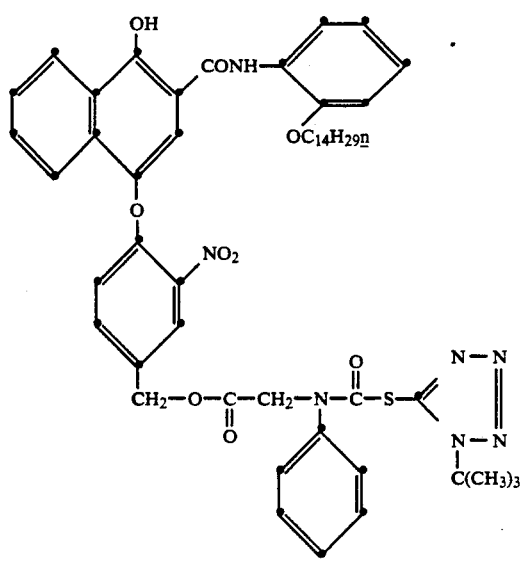
46.
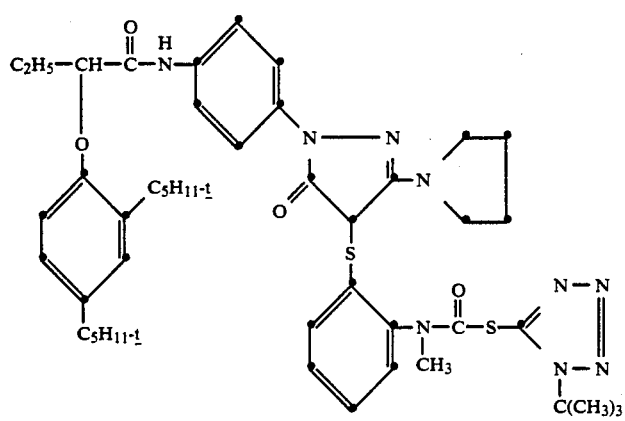
47.
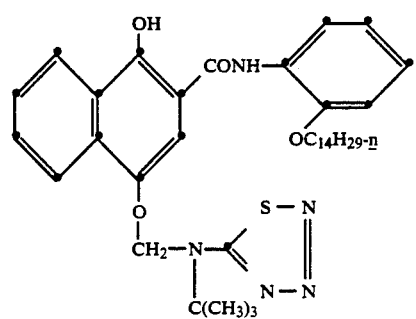
48.

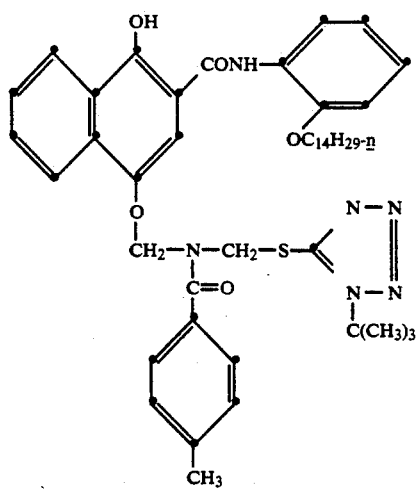
49.
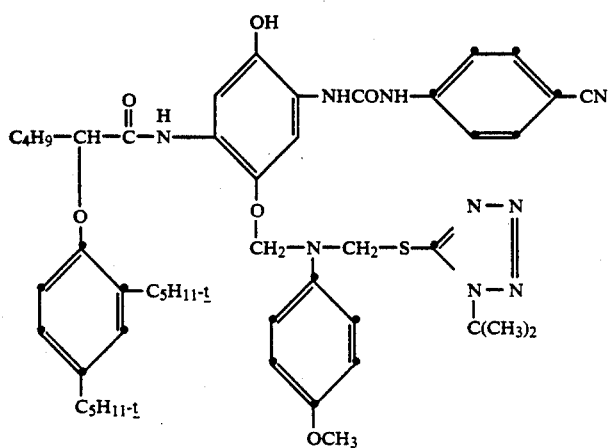
50.
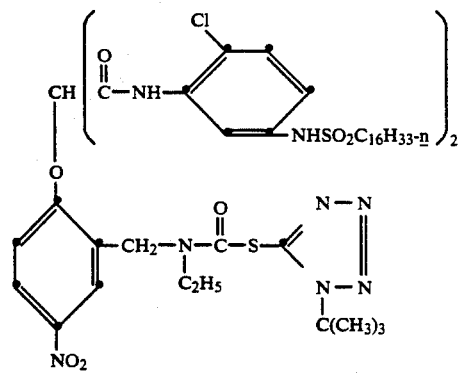
51.
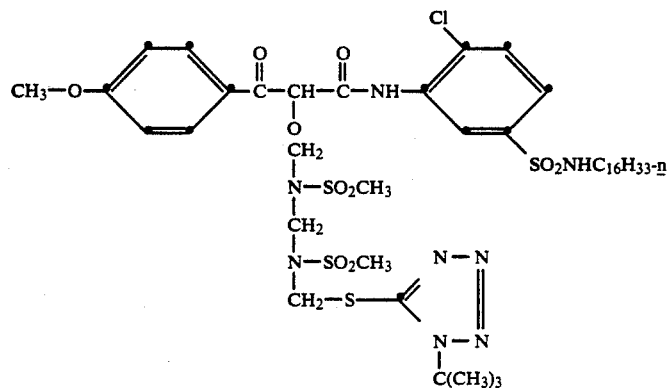
52.

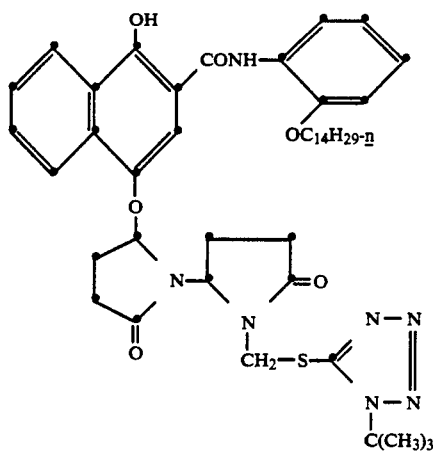
53.
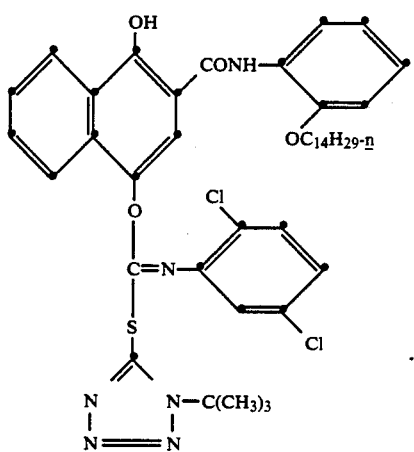
54.
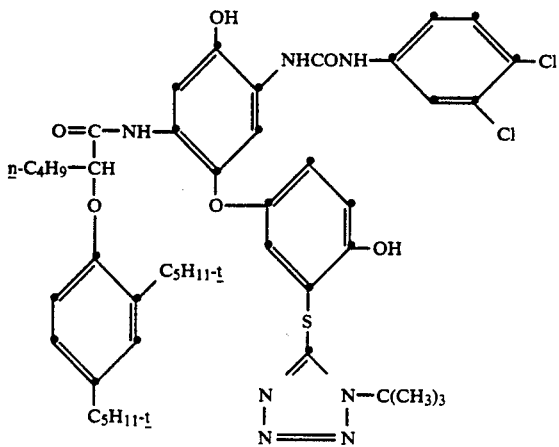
55.

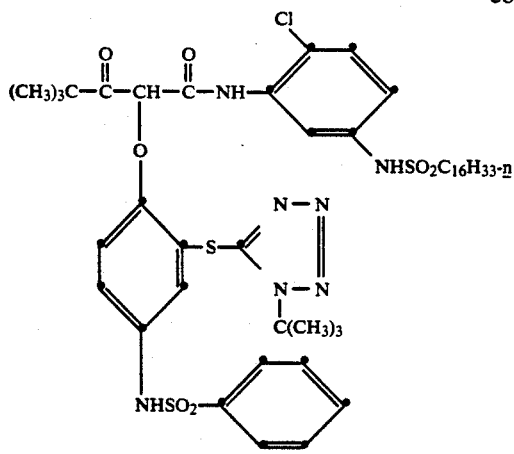
56.
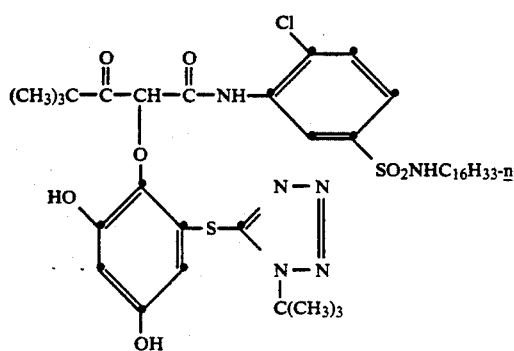
57.
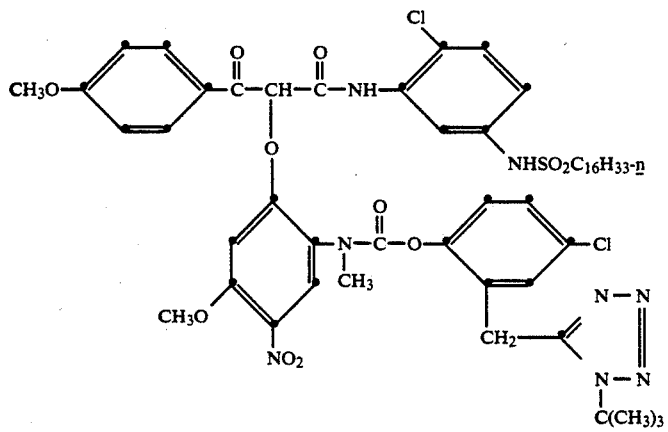
58.
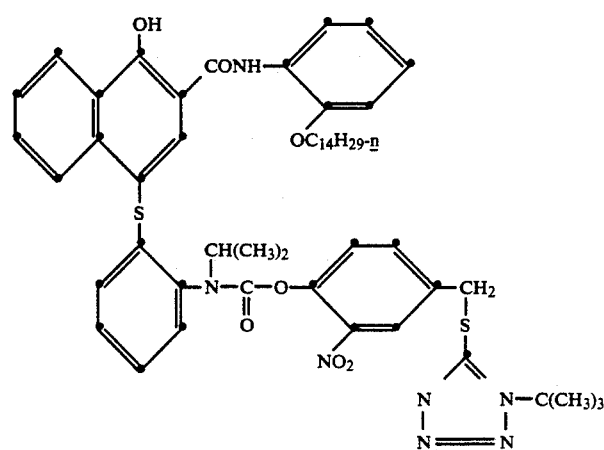
59.

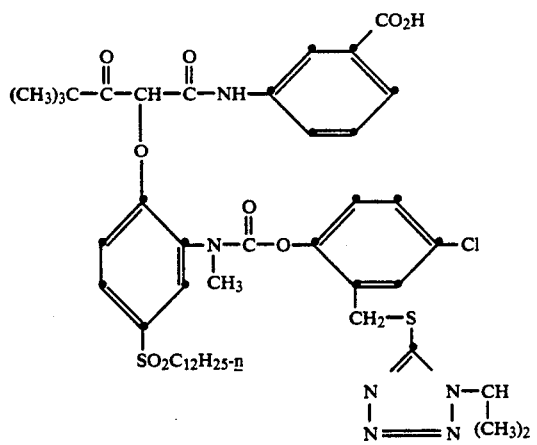
60.
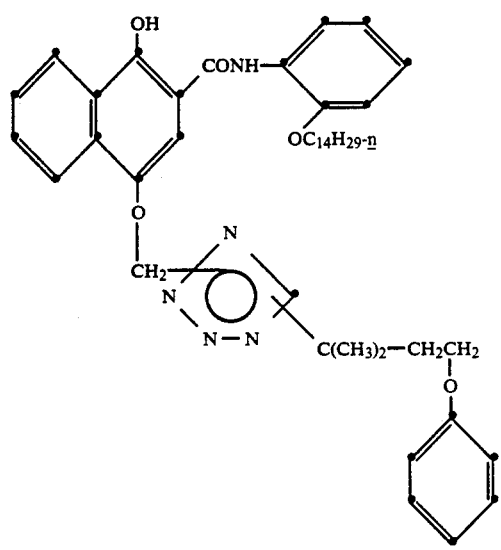
61.
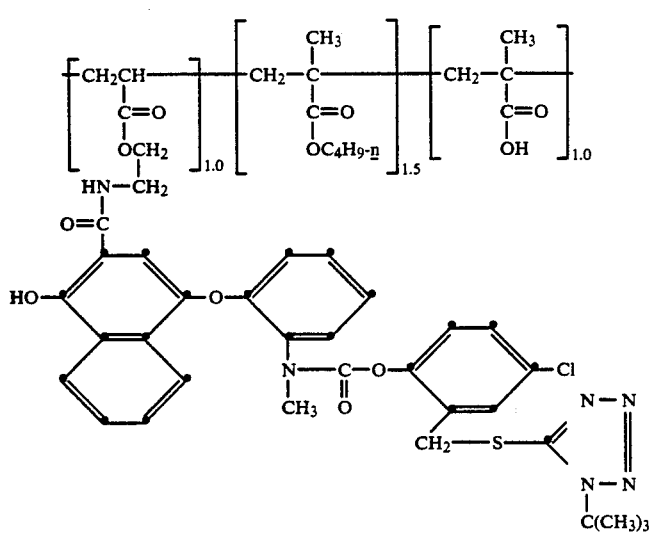
62.

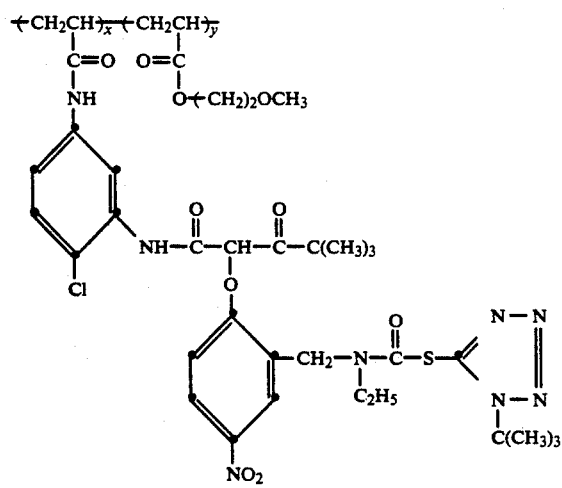
63.
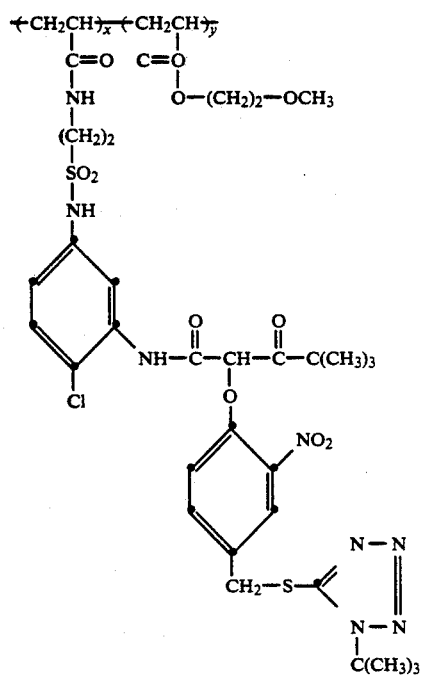
64.
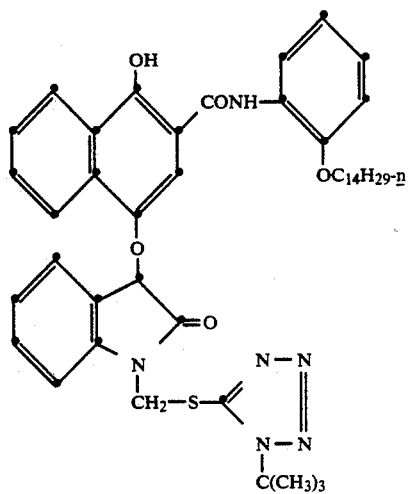
65.

66.

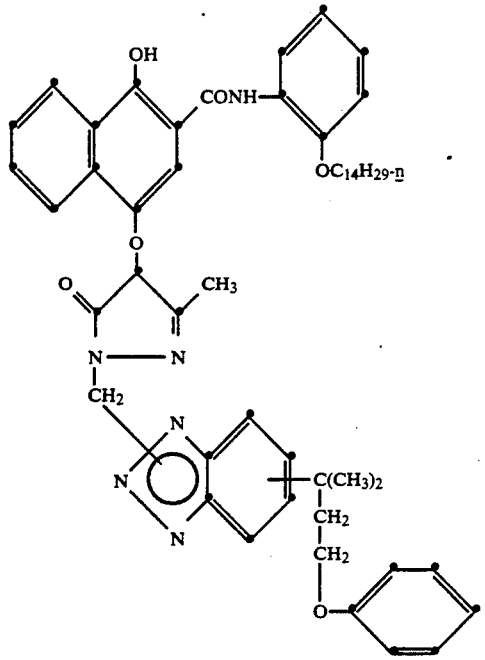

67.

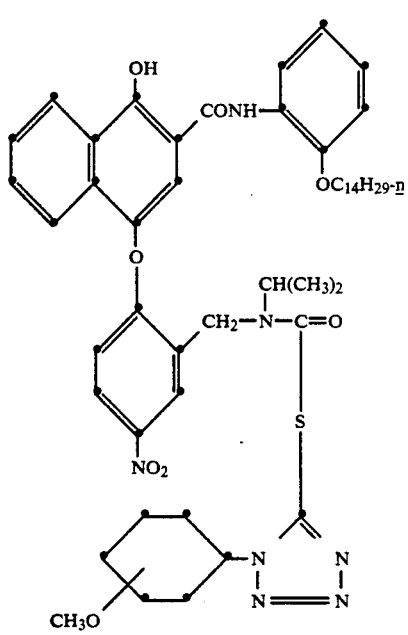

PHOTOGRAPHIC EXAMPLE

Sharpness and Interimage Effects

Nineteen color photographic materials (entries 1-19 in the Table) were prepared according to the following schematic layer structure (numerical values denote coating coverages in mg/m$^2$):

| | |
|---|---|
| Overcoat: | Gelatin - 2500; Gelatin Hardener (BVSM) 1.75% |
| Photographic Layer 1: | Green-Sensitive AgIBr - 1600; Gelatin - 2400; Cyan dye forming coupler (IC-1) - 750; ± DIR compounds (see Table). |
| Interlayer: | Antistain agent 2,5-didodecylhydroquinone - 115 Gelatin - 620. |// -continued
| Photographic Layer 2: | Red-Sensitive AgIBr - 1600; Gelatin - 2400; Yellow dye forming coupler (IC-2) - 1300. |
| Film Support | With antihalation gray silver - 324; Gelatin - 2452; Antistain agent - 15. |

Three additional color photographic materials were prepared (entries 20-22 in the Table) that differed from the first nineteen only in that Yellow dye forming coupler (IC-2) replaced Cyan dye forming coupler (IC-1) in photographic layer 1 and in that Magenta dye forming coupler (IC-3) replaced Yellow dye forming coupler (IC-2) in photographic layer 2.

The dye forming couplers IC-1 and IC-2 were each dispersed in half their weight of di-n-butyl phthalate, the dye forming coupler IC-3 was dispersed in half it's weight of tri-cresyl phosphates and the DIR compounds were each dispersed in twice their weight of diethyl lauramide.

For DIR coupler effect, the samples were exposed through a graduated-density test object and a Wratten 99 (green) filter. This exposed photographic layer 1.

For interimage evaluation, the samples were exposed through a graduated-density test object and Wratten 12 (minus blue) filter. This exposes both photographic layers equally.

For sharpness, evaluated by calculating CMT acutance values for 16 mm film (this technique is described in an article entitled: "An improved Objective Method for Rating Picture Sharpness: CMT Acutance", by R. G. Gendron, Journal of the SMPTE, 82, 1009–12, 1973), exposures were made through a Wratten 99 (green) filter.

The materials were then processed at 38° C. as follows:

| | |
|---|---|
| Color Developer | 2¼' |
| Stop (5% Acetic Acid) | 2' |
| Wash | 2' |
| Bleach KFe(CN)$_6$ | 2' |
| Fix | 2' |
| Wash | 2' |

The color developer composition was:

| | |
|---|---|
| $K_2SO_3$ | 2.0 g/l |
| 4-amino-3-methyl-N-ethyl beta-hydroxyethylanaline sulfate | 3.35" |
| $K_2CO_3$ | 30.0" |
| KBr | 1.25" |
| KI | 0.0006" |
| adjusted to pH = 10.0 | |

The oxidized color developing agent generated by development of exposed silver reacts with adjacent image dye forming compounds and DIR compounds to form dyes and to release inhibitor (or inhibitor precursor) in photographic layer 1. The development inhibiting effects of the inhibitor released from the DIR compound were assessed by monitoring the gamma of photographic layer 1. The sharpness effects of the inhibitor released from the DIR compound were assessed by monitoring the acutance of photographic layer 1. Higher values of the acutance indicate greater sharpness in the film.

The interimage effects of the inhibitor released from the DIR compound were assessed by monitoring the ratio of the gammas of photographic layer 1 (causer of interimage) and photographic layer 2 (receiver of interimage). The larger the gamma ratio, the larger the interimage effect (the degree of color correction) in the film.

Cyan Dye-Forming Coupler

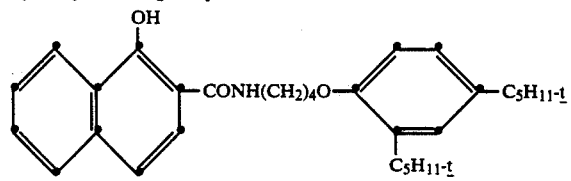

IC-1

Yellow Dye-Forming Coupler

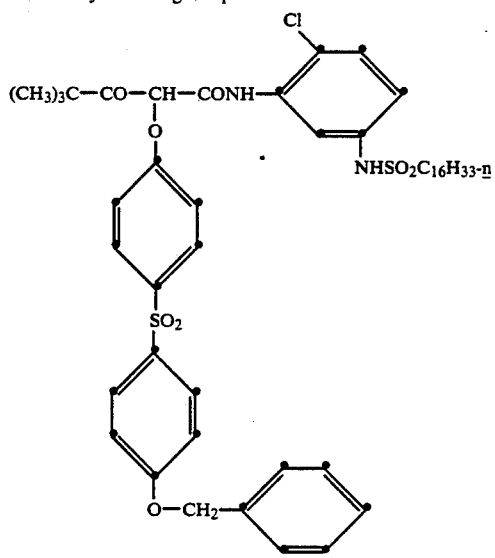

IC-2

Magenta Dye-Forming Coupler

-continued

IC-3

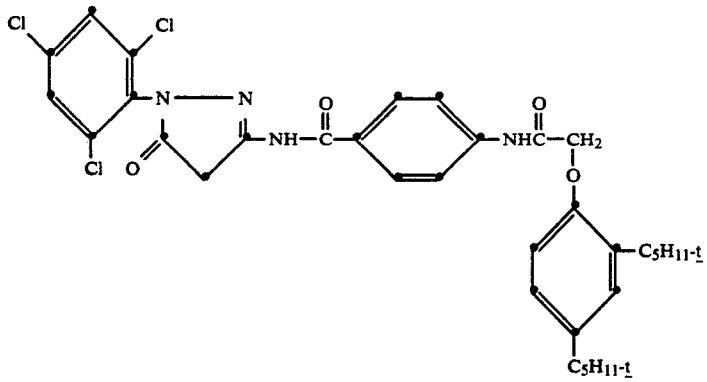

20

The Table shows the identity of the DIR compound coated, the quantity of that DIR compound (in mg/m²), the gamma of photographic layer 1 (the causer layer), the acutance of photographic layer 1, and the degree of interimage effect (color correction) of photographic layer 1 onto photographic layer 2 (causer gamma/receiver gamma).

DIR compounds A through G are known in the prior art and are comparative compounds. Table entries 1 through 15 and 20 through 22 illustrate that the DIR compounds of the invention (characterized by the combination in one DIR compound of a sterically hindered inhibitor and an intramolecular nucleophilic displacement type timing group) cause adequate degrees of intralayer development suppression and cause greater acutance an give a wider range of interimage effects than do DIR compounds of the prior art. Table entries 16 through 19 illustrate that DIR compounds of the invention (characterized by the combination in one DIR compound of a sterically hindered inhibitor and an intramolecular elimination type timing group) cause greater degrees of intralayer development suppression and cause greater acutance and give a wider range of interimage effects than do DIR compounds of the prior art.

TABLE I

| | DIR Compound | Amount (mg/m²) | Gamma "causer" | AMT | Gamma "causer Gamma "receiver" |
|---|---|---|---|---|---|
| 1 Control | none | — | 1.72 | 92.6 | 1.45 |
| 2 Control | A | 36 | 0.52 | 96.1 | 0.86 |
| 3 Control | B | 35 | 0.50 | 96.6 | 0.81 |
| 4 Control | C | 60 | 0.55 | 100.3 | 1.73 |
| 5 Invention | 14 | 66 | 0.59 | 102.2 | 0.92 |
| 6 Invention | 17 | 137 | 0.60 | 103.4 | 2.47 |
| 7 Invention | 19 | 157 | 0.50 | 102.5 | 2.13 |
| 8 Invention | 13 | 212 | 0.52 | 103.9 | 0.66 |
| 9 Invention | 12 | 107 | 0.74 | 100.6 | 2.19 |
| 10 Invention | 18 | 64 | 0.66 | 101.8 | 2.32 |
| 11 Invention | 1 | 70 | 0.65 | 102.0 | 1.10 |
| 12 Control | D | 70 | 0.65 | 96.0 | 0.65 |
| 13 Invention | 10 | 184 | 0.73 | 100.3 | 2.61 |
| 14 Invention | 13 | 180 | 0.45 | 99.4 | 1.58 |
| 15 Invention | 16 | 60 | 0.64 | 99.2 | 0.77 |
| 16 Control | E | 128 | 2.35 | 92 | 1.40 |
| 17 Control | F | 108 | 1.48 | 89.3 | 1.38 |
| 18 Invention | 4 | 132 | 0.65 | 103.1 | 1.15 |
| 19 Invention | 6 | 106 | 0.65 | 104.4 | 1.18 |
| 20 Control | none | none | 2.02 | 90.4 | 1.13 |
| 21 Control | G | 65 | 0.83 | 98.5 | 0.96 |
| 22 Invention | 32 | 135 | 0.92 | 102.3 | 1.80 |
| 23 Control | H | 60 | 0.57 | 97.3 | 1.57 |

| Control | DIR Compounds | Source |
|---|---|---|
| A |  | B of U.S. Pat. No. 4,248,962 |

-continued
| Control | DIR Compounds | Source |
|---|---|---|
| B | 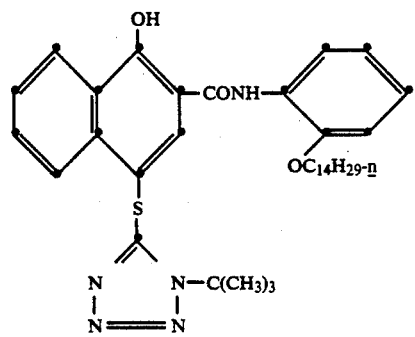 | II-53 of Jap. Kokai 59-149359 |
| C | 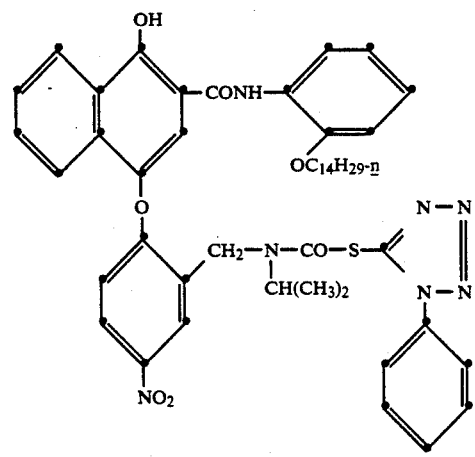 | #4 of U.S. Pat. No. 4,248,962 |
| D | 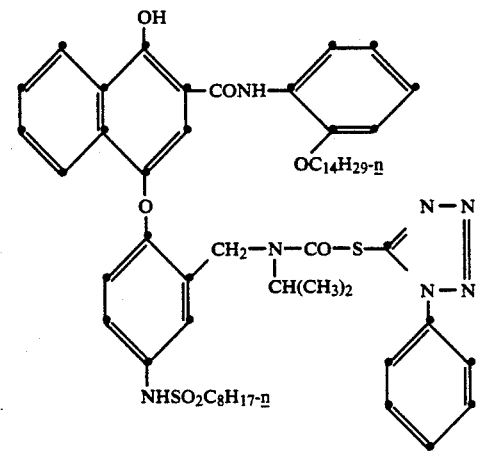 | #12 of U.S. Pat. No. 4,248,962 |

-continued
| Control | DIR Compounds | Source |
|---|---|---|
| E | 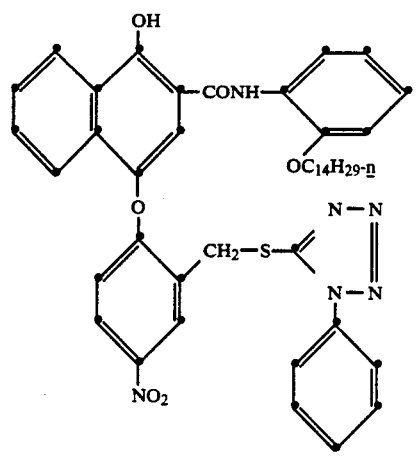 | #6 of U.S. Pat. No. 4,409,323 |
| F | 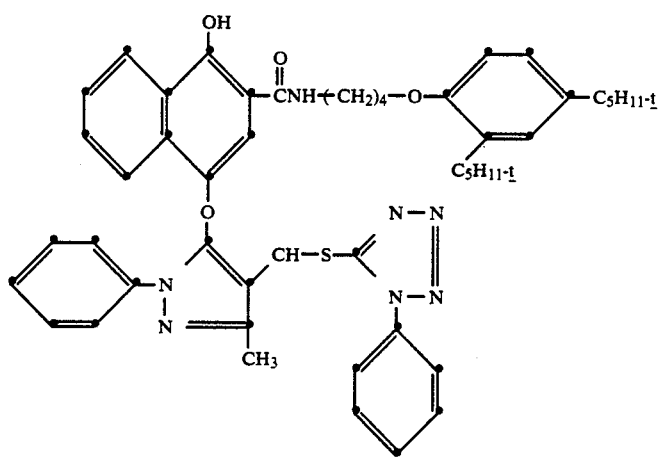 | #T-35 of U.S. Pat. No. 4,528,263 |
| G | 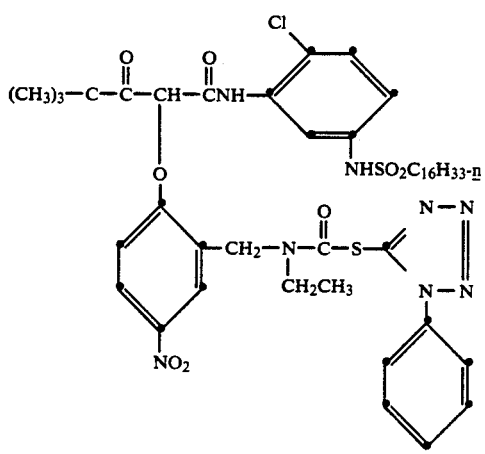 | #C-2 of EP 255,085 |

| Control DIR Compounds | Source |
|---|---|
| 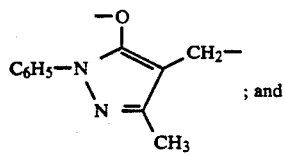 H | #21 of U.S. Pat. No. 4,248,962 |

The invention has been described in detail with particular reference to preferred embodiments thereof, but it will be understood that variations and modifications can be effected within the spirit and scope of the invention.

What is claimed is:

1. A photographic element comprising a support and at least one silver halide emulsion layer having associated therewith at least one compound (I) having a carrier moiety (CAR) and a releasable development inhibitor (INH) capable of being released during photographic processing of the element by means of at least one timing group (T) bonded to and releasable from the carrier moiety, wherein the releasable development inhibitor moiety (INH) comprises ($R^1$) a non-aromatic, sterically hindered substituent group having (a) a tertiary carbon atom bonded directly to the releasable development inhibitor moiety or (b) a secondary carbon atom bonded directly to the releasable development inhibitor wherein the secondary carbon atom is not part of an unsubstituted carbocyclic ring containing at least 6 carbon atoms;

wherein the timing group (T) is other than a pyrazolone group of the formula

wherein the combination of the timing group (T) and the development inhibitor (INH) enable increased acutance and interimage effects upon exposure and processing of the element.

2. A photographic element as in claim 1 comprising a support and at least one silver halide emulsion layer having associated therewith at least one compound (I) having a carrier moiety (CAR) and a releasable development inhibitor (INH) capable of being released during photographic processing of the element by an intramolecular nucleophilic displacement reaction, wherein the releasable development inhibitor moiety (INH) comprises ($R^1$) a non-aromatic, sterically hindered substituent group having (a) a tertiary carbon atom bonded directly to the releasable development inhibitor moiety or (b) a secondary carbon atom bonded directly to the releasable development inhibitor moiety and wherein the secondary carbon atom is not part of an unsubstituted carbocyclic ring containing at least 6 carbon atoms.

3. A photographic element as in claim 1 wherein the compound (I) having a carrier moiety is represented by the formula:

$$CAR-Nu-X-E-INH-R^1$$

wherein
CAR is a carrier moiety;
INH is a development inhibitor moiety containing at least one hetero atom;
Nu is a nucleophilic group attached to CAR at a position from which it is capable of being displaced as a result of reaction of CAR with oxidized color developing agent;
X is a linking group spatially relating Nu and E, upon displacement of Nu from CAR, enabling an intramolecular nucleophilic displacement reaction that cleaves the bond between INH and E;
E is an electrophilic group attached to a hetero atom in INH; and
$R^1$ is a non-aromatic, sterically hindered substituent group having
  a) a tertiary carbon atom bonded directly to INH; or
  b) a secondary carbon atom bonded directly to INH and wherein the secondary carbon atom is not part of an unsubstituted carbocyclic ring containing at least 6 carbon atoms.

4. A photographic element as in claim 1 wherein the non-aromatic, sterically hindered substituent group is a tertiary alkyl group.

5. A photographic element as in claim 1 wherein the carrier moiety (CAR) is a dye-forming coupler.

6. A photographic element as in claim 1 wherein the releasable development inhibitor (INH) comprising $R^1$ is:

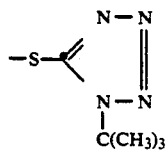

7. A photographic element as in claim 1 wherein the compound (I) having a carrier moiety is represented by the formula:

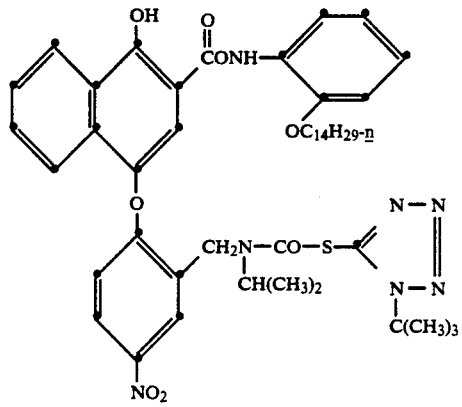

8. A photographic element as in claim 1 wherein the compound (I) having a carrier moiety is represented by the formula:

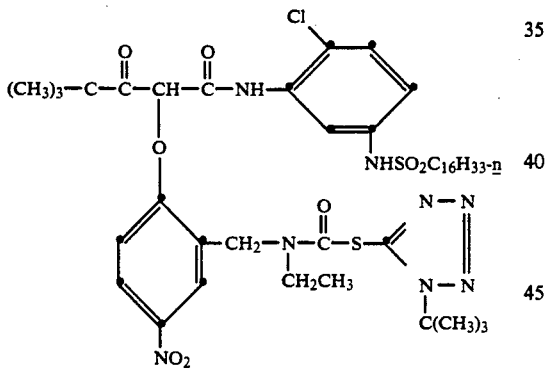

9. A photographic element comprising a support having thereon at least one red-sensitive silver halide emulsion layer having associated therewith a cyan dye-providing material, at least one green-sensitive silver halide emulsion layer having associated therewith a magenta dye-providing material, and at least one blue-sensitive silver halide emulsion layer having associated therewith a yellow dye-providing material, wherein at least one of said emulsion layers has associated therewith at least one compound (I) having a carrier moiety (CAR) and a releasable development inhibitor (INH) capable of being released by a intramolecular nucleophilic displacement reaction, wherein the releasable development inhibitor moiety (INH) comprises ($R^1$) a non-aromatic, sterically hindered substituent group having (a) a tertiary carbon atom bonded directly to the releasable development inhibitor moiety or (b) a secondary carbon atom bonded directly to the releasable development inhibitor moiety and wherein the secondary carbon atom is not part of an unsubstituted carbocyclic ring containing at least 6 carbon atoms.

10. A photographic element as in claim 9 wherein the releasable development inhibitor (INH) comprising ($R^1$) is:

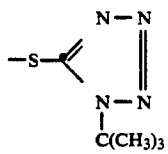

11. A photographic element as in claim 9 wherein the compound having a carrier moiety is represented by the formula:

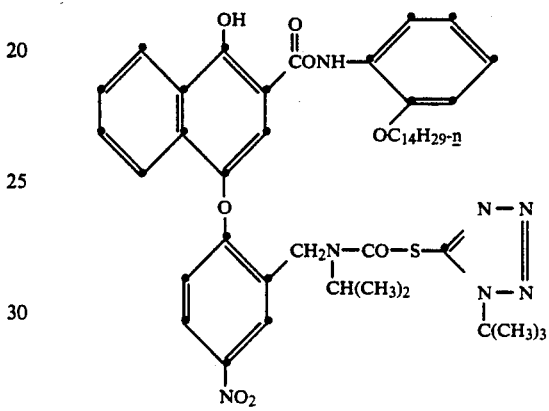

12. A photographic element as in claim 9 wherein the compound having a carrier moiety is represented by the formula:

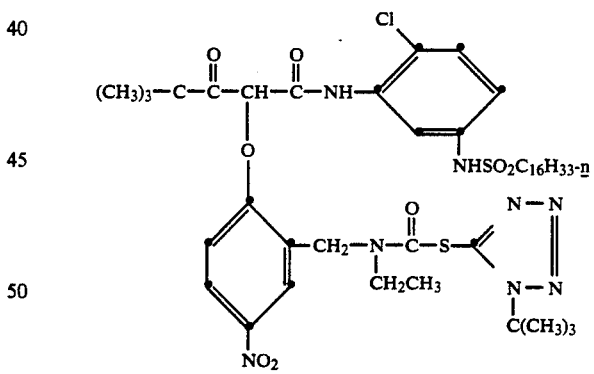

13. A process of developing an image in an exposed photographic element comprising a support and at least one silver halide emulsion layer containing an imagewise distribution of developable silver halide grains, wherein the process comprises the step of developing the element with a silver halide color developing agent in the presence of at least one photographic coupler and at least one compound (I) having a carrier moiety (CAR) and a releasable development inhibitor (INH) capable of being released during photographic processing of the element by means of at least one timing group (T);

wherein the timing group (T) is other than a pyrazolone group of the formula

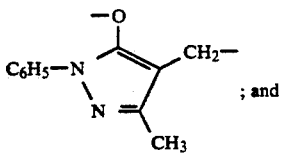
; and wherein the releasable development inhibitor moiety (INH) comprises (R¹) a non-aromatic, sterically hindered substituent group having (a) a tertiary carbon atom bonded directly to the releasable development inhibitor moiety or (b) a secondary carbon atom bonded directly to the releasable development inhibitor moiety wherein the secondary carbon atom is not part of an unsubstituted carbocyclic ring containing at least 6 carbon atoms;

wherein the combination of timing group (T) and the development inhibitor moiety (INH) enable increased acutance and interimage effect upon processing of the element.

14. A process as in claim 13 of developing an image in an exposed photographic element comprising a support and at least one silver halide emulsion layer containing an imagewise distribution of developable silver halide grains, wherein the process comprises the step of developing the element with a silver halide color developing agent in the presence of at least one photographic coupler and at least one compound (I) having a carrier moiety (CAR) and a releasable development inhibitor moiety (INH) capable of being released by an intramolecular nucleophilic displacement reaction wherein the releasable development inhibitor moiety (INH) comprises (R¹) a non-aromatic, sterically hindered substituent group having (a) a tertiary carbon atom bonded directly to the releasable development inhibitor moiety or (b) a secondary carbon atom bonded directly to the releasable development inhibitor moiety and wherein the secondary carbon atom is not part of an unsubstituted carbocyclic ring containing at least 6 carbon atoms.

15. A process as in claim 13 wherein the non-aromatic, sterically hindered substituent group is a tertiary alkyl group.

16. A process as in claim 13 wherein the releasable development inhibitor moiety (INH) comprising (R¹) is:

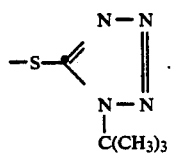

* * * * *